(12) United States Patent
Watanabe

(10) Patent No.: US 11,099,248 B2
(45) Date of Patent: Aug. 24, 2021

(54) CONTACT AVOIDANCE APPARATUS AND MEDICAL APPARATUS

(71) Applicant: General Electric Company, Schenectady, NY (US)

(72) Inventor: Motoki Watanabe, Hino (JP)

(73) Assignee: General Electric Company, Schenectady, NY (US)

( * ) Notice: Subject to any disclaimer, the term of this patent is extended or adjusted under 35 U.S.C. 154(b) by 50 days.

(21) Appl. No.: 16/179,574

(22) Filed: Nov. 2, 2018

(65) Prior Publication Data

US 2019/0162799 A1 May 30, 2019

(30) Foreign Application Priority Data

Nov. 30, 2017 (JP) .............................. JP2017-230671

(51) Int. Cl.
*G01R 33/30* (2006.01)
*G01R 33/28* (2006.01)
*A61B 6/00* (2006.01)
*A61B 6/04* (2006.01)
*G01R 33/54* (2006.01)
*A61B 5/055* (2006.01)

(52) U.S. Cl.
CPC ............ *G01R 33/307* (2013.01); *A61B 5/055* (2013.01); *A61B 6/0492* (2013.01); *A61B 6/547* (2013.01); *G01R 33/543* (2013.01); *G01R 33/288* (2013.01)

(58) Field of Classification Search
None
See application file for complete search history.

(56) References Cited

U.S. PATENT DOCUMENTS 5,485,502 A * 1/1996 Hinton ................... A61B 6/102
250/363.01
5,570,770 A * 11/1996 Baaten ................... A61B 6/102
192/129 A (Continued)

FOREIGN PATENT DOCUMENTS

JP      2007089674 A  *  4/2007  ............... A61B 6/03
JP      2014-161392 A     9/2014

(Continued)

OTHER PUBLICATIONS

CN107242866A, Shang Gao, Medical Equipment and Method for Controlling Motion of Medical Equipment (Part 1 of 2) [See also U.S. Publication No. 2018/0321684 A1], Oct. 13, 2017 (Year: 2017).*

(Continued)

*Primary Examiner* — Jermele M Hollington

(57) ABSTRACT

A CT apparatus comprises; a sensor section outputting distance data for determining a distance between the sensor section and at least part of a subject to be examined laid on a cradle; contour-data generating means for generating contour data representing a contour of the at least part of the subject based on the distance data obtained from the sensor section; and deciding means for deciding whether or not there is a risk for said subject to come into contact with said gantry while said gantry or said table is moving based on data representing a limit of a range up to which said subject can come close to the gantry and on said contour data.

8 Claims, 18 Drawing Sheets

(56) References Cited

U.S. PATENT DOCUMENTS

| | | | | |
|---|---|---|---|---|
| 6,651,279 | B1* | 11/2003 | Muthuvelan | A61B 6/0457 5/600 |
| 7,857,513 | B2* | 12/2010 | Li | A61B 6/032 378/195 |
| 8,378,325 | B2* | 2/2013 | Fadler | A61N 5/1081 250/505.1 |
| 9,433,387 | B2* | 9/2016 | Ahn | A61N 5/1049 |
| 10,272,265 | B2* | 4/2019 | Filiberti | A61N 5/1049 |
| 10,299,740 | B2* | 5/2019 | Mc Carthy | A61B 6/4435 |
| 10,610,307 | B2* | 4/2020 | Kotian | H04N 5/247 |
| 10,799,719 | B2* | 10/2020 | Cho | A61N 5/1067 |
| 2004/0120467 | A1* | 6/2004 | Wollenweber | A61B 6/04 378/206 |
| 2004/0172757 | A1* | 9/2004 | Somasundaram | A61B 6/105 5/601 |
| 2007/0251008 | A1* | 11/2007 | Li | A61B 6/547 5/601 |
| 2008/0025459 | A1* | 1/2008 | Shi | A61B 6/032 378/10 |
| 2008/0091101 | A1* | 4/2008 | Velusamy | A61B 6/032 600/427 |
| 2008/0187097 | A1* | 8/2008 | Cheng | B25J 9/1666 378/65 |
| 2009/0209852 | A1* | 8/2009 | Mate | A61B 90/14 600/431 |
| 2011/0006230 | A1 | 1/2011 | Fadler | |
| 2014/0184218 | A1* | 7/2014 | Heukensfeldt Jansen | G01R 33/543 324/309 |
| 2014/0208510 | A1* | 7/2014 | Iizuka | A61B 6/0407 5/601 |
| 2014/0210470 | A1* | 7/2014 | Xu | G01R 33/28 324/309 |
| 2016/0302871 | A1* | 10/2016 | Gregerson | A61B 34/30 |
| 2017/0086758 | A1* | 3/2017 | Mc Carthy | A61B 6/542 |
| 2017/0316562 | A1* | 11/2017 | Haberland | G06T 7/0012 |
| 2018/0321684 | A1* | 11/2018 | Gao | G05D 1/0223 |
| 2019/0059843 | A1* | 2/2019 | Watanabe | H05G 1/26 |
| 2019/0090954 | A1* | 3/2019 | Kotian | A61B 34/20 |
| 2019/0130598 | A1* | 5/2019 | Chikamatsu | G06T 7/70 |
| 2020/0405256 | A1* | 12/2020 | Dickmann | A61B 6/102 |

FOREIGN PATENT DOCUMENTS

| | | | | |
|---|---|---|---|---|
| JP | 2014161392 A | * | 9/2014 | A61B 6/03 |
| JP | 2005013489 A | | 1/2015 | |
| JP | 2019097775 A | * | 6/2019 | A61B 6/0492 |

OTHER PUBLICATIONS

CN107242866A, Shang Gao, Medical Equipment and Method for Controlling Motion of Medical Equipment (Part 2 of 2) [See also U.S. Publication No. 2018/0321684 A1], Oct. 13, 2017 (Year: 2017).*
Translation of JP2007089674 filed Apr. 12, 2007 (Year: 2007).*
JP Office Action for Corresponding application No. 2017-230671, Office Action dated Jul. 24, 2018; 5 pages.
Notice of Allowance for corresponding JP application No. 2017-230671, dated Mar. 19, 2019, 3 pages.

* cited by examiner

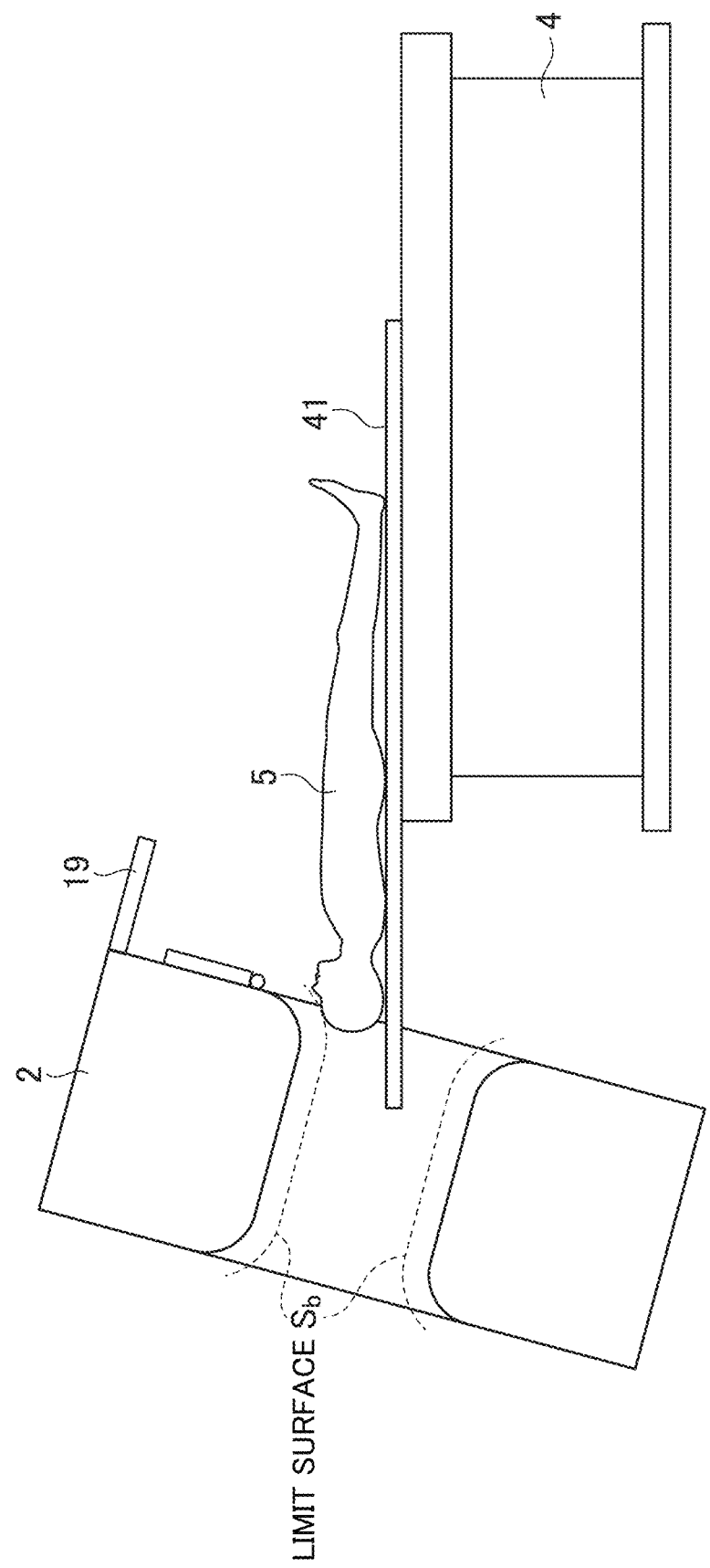

CONTACT AVOIDANCE APPARATUS AND MEDICAL APPARATUS

FIELD OF THE INVENTION

The present invention relates to a contact avoidance apparatus for avoiding contact of a subject to be examined laid on a cradle of a table with a gantry, a medical apparatus having the contact avoidance apparatus, and a program applied to the contact avoidance apparatus.

BACKGROUND OF THE INVENTION

Medical apparatuses, such as a CT (Computed Tomography) apparatus and an MRI (Magnetic Resonance Imaging) apparatus, are known as apparatuses for acquiring an image of the inside of a subject to be examined. Since the CT and MRI apparatuses are capable of non-invasively imaging the subject, they are used as apparatuses indispensable in diagnosing the subject's health.

On the other hand, in imaging the subject with the CT apparatus and MRI apparatus, a radiographer has to carry out various tasks for preparing a scan, which poses a problem that radiographers experience a lot of work stress. Accordingly, to mitigate the radiographers' work stress, there is disclosed a technique of automatically operating a table of a CT apparatus (see PTL 1).

According to Japanese Patent Application Publication No. 2014-161392, a table can be automatically operated, which makes it possible to mitigate the radiographers' work stress.

On the other hand, a cradle of the table has the subject laid thereon. Therefore, it is necessary to avoid contact of the subject with the gantry while actuating the table to move the subject toward a bore of the gantry. Especially in the case that the table is automatically operated, it is important to provide the CT apparatus with means for avoiding contact between the subject and the gantry. The CT apparatus described in PTL 1, however, has no such contact avoidance means. Therefore, according to PTL 1, while moving the subject toward the bore of the gantry, the operator has to pay attention to motion of the table with his/her hand constantly placed on a stop button of the gantry so that he/she can promptly stop movement of the table when the subject is about to collide with the gantry; this poses a problem that radiographers' work stress is difficult to fully mitigate.

Therefore, there is a need for a technique capable of automatically avoiding contact between the subject and the gantry.

BRIEF DESCRIPTION OF THE INVENTION

A first aspect of the present invention is a contact avoidance apparatus for avoiding contact of a subject to be examined laid on a cradle of a table with a gantry, said apparatus comprising:
a sensor section for acquiring distance data for determining a distance between said sensor section and at least part of said subject laid on said cradle;
contour-data generating means for generating contour data representing a contour of said at least part of said subject, wherein the contour-data generating means determines information on positions of points on a body surface of said at least part of said subject with respect to said cradle based on said distance data, and generates said contour data based on said information on positions; and deciding means for deciding whether or not there is a risk for said subject to come into contact with said gantry while said gantry or said table is moving based on data representing a limit of a range up to which said subject can come close to said gantry and on said contour data.

A second aspect of the present invention is a medical apparatus comprising:
a gantry;
a cradle on which a subject to be examined is laid;
a sensor section for acquiring distance data for determining a distance between said sensor section and at least part of said subject laid on said cradle;
contour-data generating means for generating contour data representing a contour of said at least part of said subject, wherein the contour-data generating means determines information on positions of points on a body surface of said at least part of said subject with respect to said cradle based on said distance data, and generates said contour data based on said information on positions; and
deciding means for deciding whether or not there is a risk for said subject to come into contact with said gantry while said gantry or said table is moving based on data representing a limit of a range up to which said subject can come close to said gantry and on said contour data.

A third aspect of the present invention is a program applied to a contact avoidance apparatus for avoiding contact of a subject to be examined laid on a cradle with a gantry using distance data for determining a distance between a sensor section and at least part of said subject laid on said cradle, said program being for causing a computer to execute:
contour-data generating processing of generating contour data representing a contour of said at least part of said subject, wherein the contour-data generating processing determines information on positions of points on a body surface of said at least part of said subject with respect to said cradle based on said distance data, and generates said contour data based on said information on positions; and
deciding processing of deciding whether or not there is a risk for said subject to come into contact with said gantry while said gantry or said table is moving based on data representing a limit of a range up to which said subject can come close to said gantry and on said contour data.

Contour data representing a contour of the subject is generated. Therefore, by using data representing a limit of a range up to which the subject can come close to the gantry and the contour data, it is possible to recognize whether or not the subject is approaching beyond the range up to which the subject can come close to the gantry. Thus, it is possible to decide whether or not there is a risk for the subject to come into contact with the gantry.

BRIEF DESCRIPTION OF DRAWINGS

FIG. 18 is an explanatory diagram for contact avoidance in the case that the gantry 2 is provided with a tilt mechanism.

DETAILED DESCRIPTION OF THE INVENTION

Now embodiments for practicing the invention will be described hereinbelow, although the present invention is not limited to the following embodiments.

Figure 1:
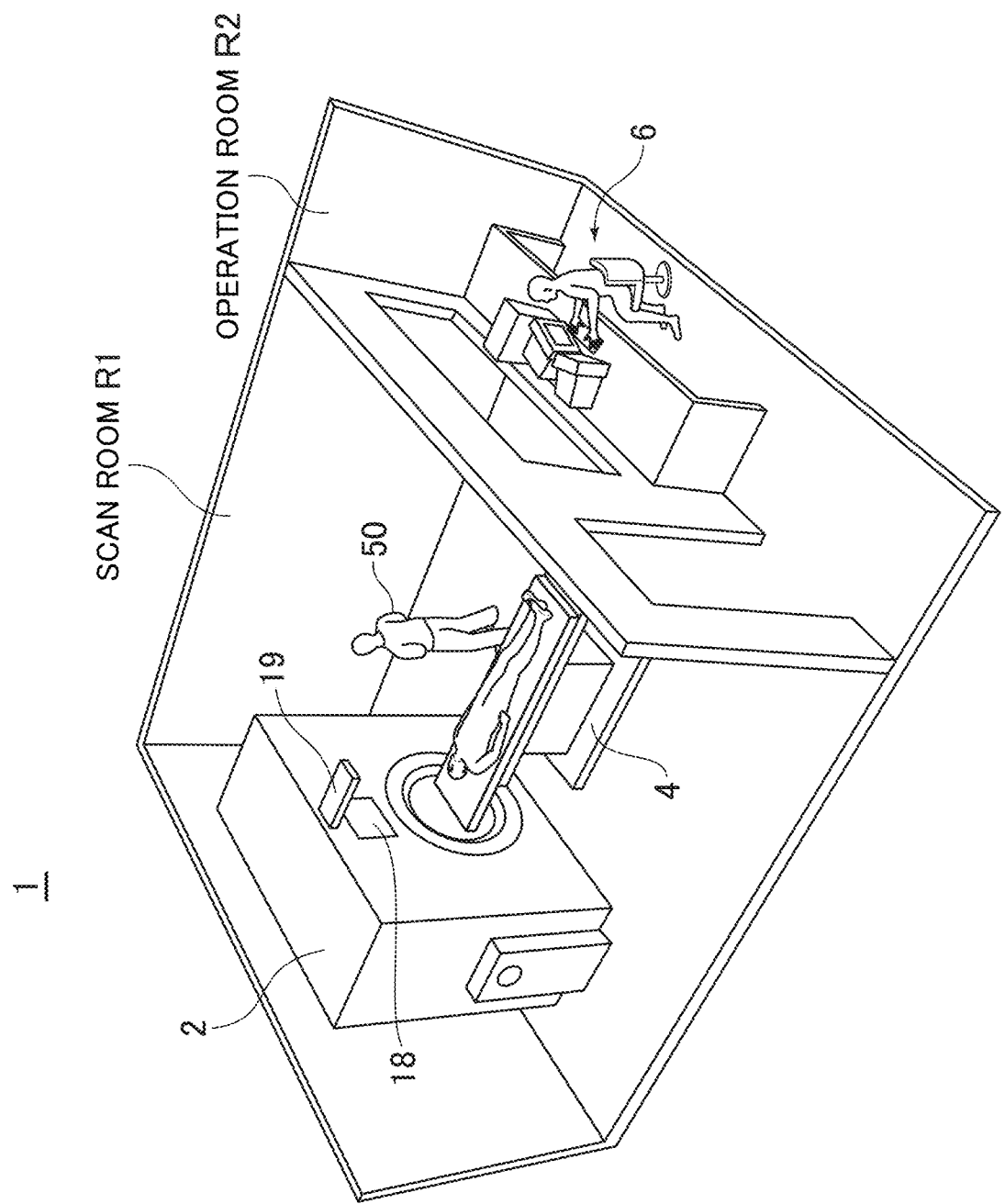
FIG. 1 is an external view of an X-ray CT apparatus in a first embodiment.

FIG. 1 is an external view of an X-ray CT apparatus in a first embodiment.

As shown in FIG. 1, the X-ray CT apparatus 1 comprises a gantry 2, a table 4, and an operation console 6.

The gantry 2 and table 4 are installed in a scan room R1. The operation console 6 is installed in an operation room R2 different from the scan room R1.

The gantry 2 is provided on its front surface with a sensor section 19 and a display section 18. The sensor section 19 and display section 18 will be discussed later.

Figure 2:
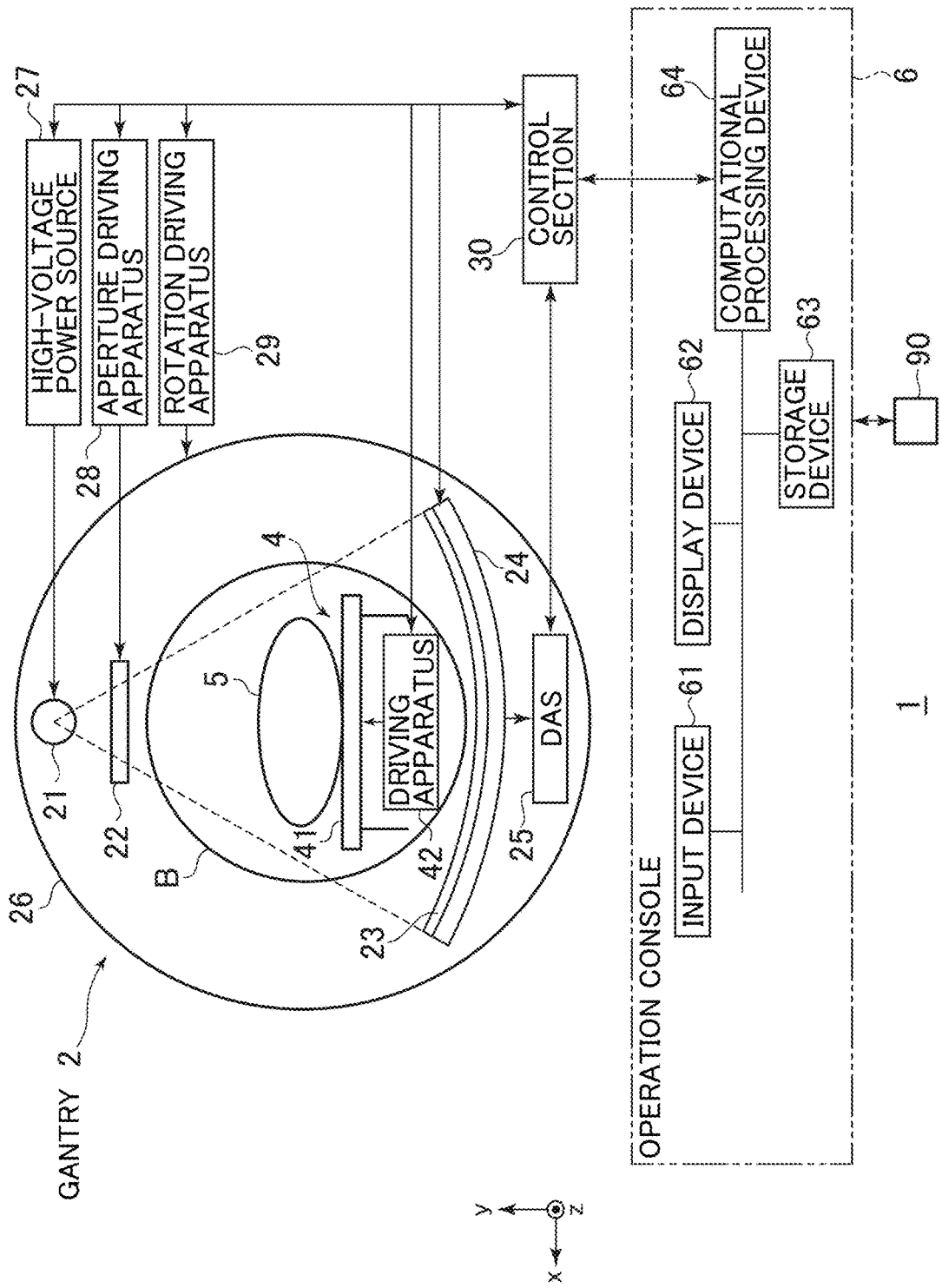
FIG. 2 is a diagram schematically showing a hardware configuration of the X-ray CT apparatus 1 in accordance with the first embodiment.

FIG. 2 is a diagram schematically showing a hardware configuration of the X-ray CT apparatus 1 in accordance with the first embodiment.

The gantry 2 has an X-ray tube 21, an aperture 22, a collimator device 23, an X-ray detector 24, a data acquisition system (DAS) 25, a rotating section 26, a high-voltage power source 27, an aperture drive apparatus 28, a rotation drive apparatus 29, and a gantry/table control section 30. In FIG. 2, the sensor section 19 and display section 18 provided on the front surface of the gantry 2 are omitted in the drawing.

The X-ray tube 21, aperture 22, collimator device 23, X-ray detector 24, and data acquisition system 25 are mounted on the rotating section 26.

The X-ray tube 21 and X-ray detector 24 are disposed to face each other sandwiching an imaging volume, i.e., a bore B of the gantry 2, in which a subject 5 to be examined is placed.

The aperture 22 is disposed between the X-ray tube 21 and bore B. The aperture 22 shapes X-rays emitted from an X-ray focus of the X-ray tube 21 toward the X-ray detector 24 into a fan beam or a cone beam.

The collimator device 23 is disposed between the bore B and X-ray detector 24. The collimator device 23 removes scatter rays that would otherwise impinge upon the X-ray detector 24.

The X-ray detector 24 has a plurality of X-ray detector elements two-dimensionally arranged in directions of the span and the thickness of the fan-shaped X-ray beam emitted from the X-ray tube 21. The X-ray detector elements each detect X-rays passing through the subject 5 placed in the bore B, and output electric signals depending upon their intensity.

The data acquisition system 25 receives the electric signals output from the X-ray detector elements in the X-ray detector 24, and converts them into X-ray data for collection.

The table 4 has a cradle 41 and a drive apparatus 42. The subject 5 is laid on the cradle 41. The drive apparatus 42 drives the table 4 and cradle 41 so that the cradle 41 is movable in y- and z-directions.

The high-voltage power source 27 supplies high voltage and electric current to the X-ray tube 21.

The aperture drive apparatus 28 drives the aperture 22 to modify the shape of its opening.

The rotation drive apparatus 29 rotationally drives the rotating section 26.

The gantry/table control section 30 controls several apparatuses and sections in the gantry 2, the drive apparatus 42, etc.

The gantry 2 also has the display section (referred to as "gantry display section hereinbelow) 18 and the sensor section 19 in an upper portion of its surface on the side of the table 4 installed.

Figure 3:
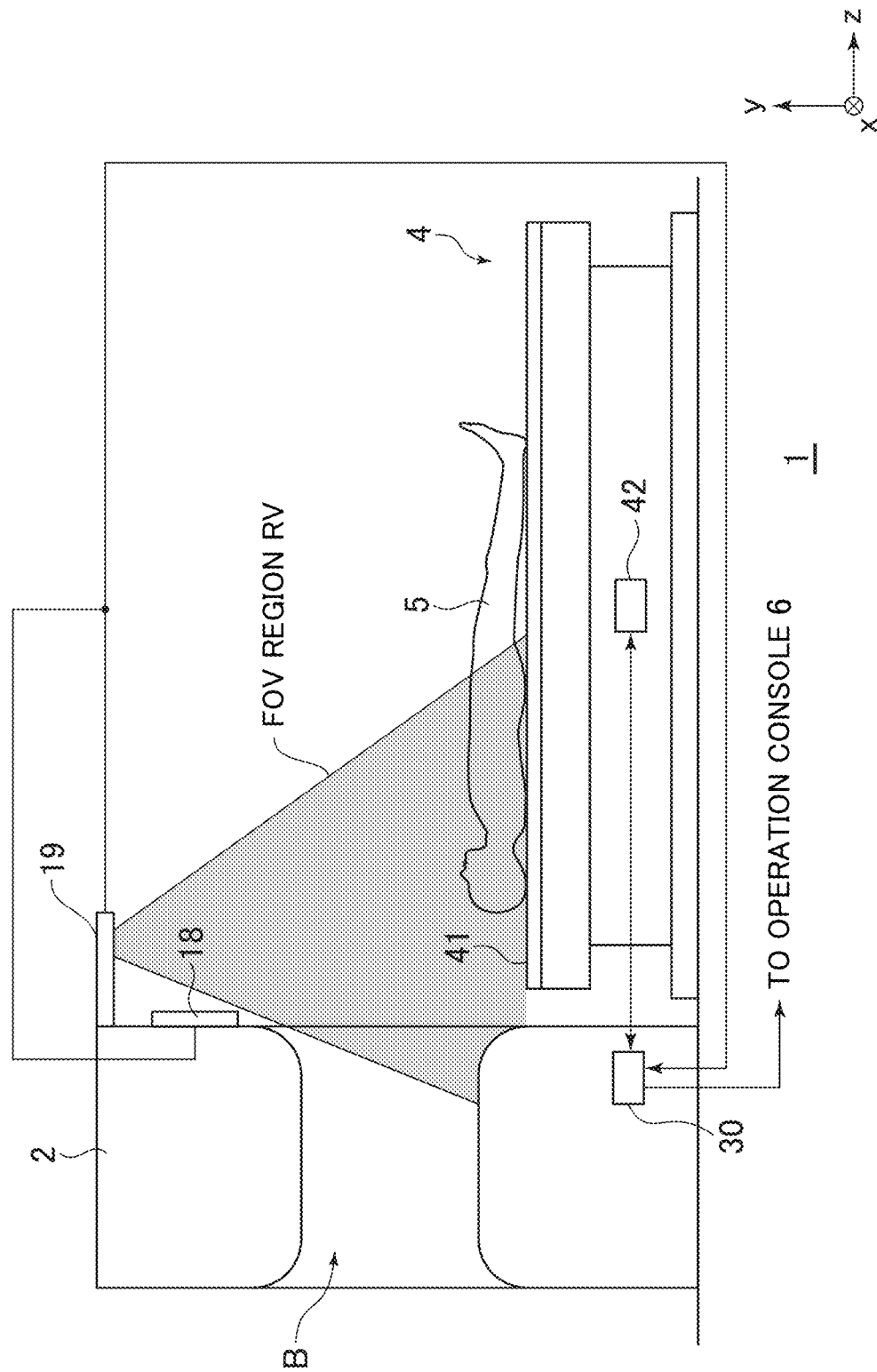
FIG. 3 is an explanatory diagram for a sensor section 19 and a gantry display section 18.

FIG. 3 is an explanatory diagram for the sensor section 19 and gantry display section 18. FIG. 3 shows a side view of the gantry 2 and table 4.

The gantry display section 18 has a display with touch-panel-driven GUI (Graphical User Interface). The gantry display section 18 is connected to the operation console 6 via the gantry/table control section 30. A radiographer 50 performs a touch-panel operation on the gantry display section 18, whereby he/she can achieve several kinds of operations and settings related to the X-ray CT apparatus 1. The gantry display section 18 can also display several kinds of setting screens, graph displays, images, etc., on its display.

The sensor section 19 has a number of pixels of n by m, and is configured to acquire image data and distance data. The numbers n and m are, for example, n=640 and m=480. Each pixel in the sensor section 19 has an imaging section for acquiring the image data.

The imaging section is a CCD (Charge Coupled Device) for acquiring color information in, for example, RGB (Red Green Blue), or a monochrome CCD. The imaging section outputs the image data for the subject 5 laid on the cradle 41 of the table 4.

In addition to the imaging section described above, each pixel in the sensor section 19 is provided with a light receiving section for acquiring the distance data. The light receiving section receives reflected rays of infrared rays emitted from an infrared source provided in the sensor section 19 toward the subject 5, and based on the received reflected rays, outputs the distance data for determining a distance between the sensor section 19 and each position on the surface of the subject 5. The sensor section 19 that may be used is, for example, a TOF camera manufactured by Panasonic Photo & Lighting Co., Ltd. It should be noted that infrared rays may be replaced with ultrasound or laser light for use to acquire the distance data.

In FIG. 3, a range of a field of view of the sensor section 19 is defined so that the portion of the table 4 on the side of the gantry 2 falls within a field-of-view region RV while the portion of the table 4 on the side opposite to the gantry 2 falls outside the field-of-view region RV. However, the field-of-view region RV of the sensor section 19 may be defined so that the whole table 4 falls within the field-of-view region RV.

The gantry/table control section 30 drives the drive apparatus 42 as needed based on input signals from the gantry display section 18 and/or sensor section 19.

Returning to FIG. 2, the explanation will be continued below.

The operation console 6 accepts several kinds of operations from the radiographer. The operation console 6 has an input device 61, a display device 62, a storage device 63, and a computational processing device 64.

As used herein, a direction of the body axis of the subject 5, i.e., a direction of carrying of the subject 5 by the table 4 will be referred to as z-direction. A vertical direction will be referred to as y-direction, and a horizontal direction orthogonal to the y- and z-directions will be referred to as x-direction.

Figure 4:
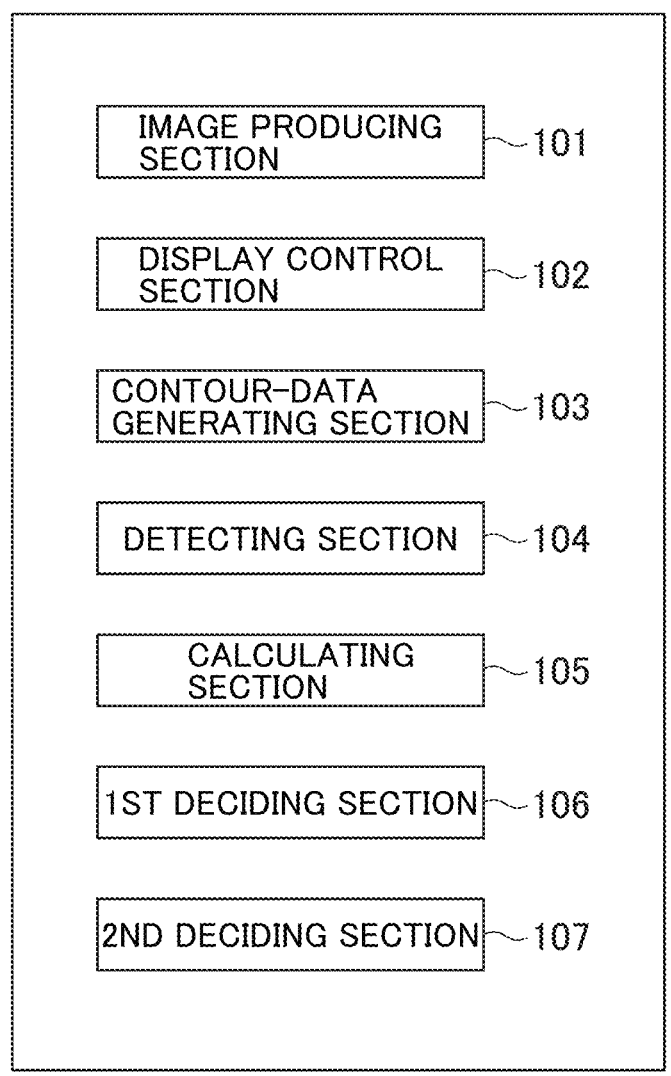
FIG. 4 is a block diagram of main functions of the X-ray CT apparatus.

FIG. 4 is a block diagram of main functions of the X-ray CT apparatus. While in practice, the X-ray CT apparatus has a large number of functional blocks, only those necessary in the explanation of the first embodiment are shown here.

In the first embodiment, the X-ray CT apparatus has, as its main functional blocks, an image producing section 101, a display control section 102, a contour-data generating section 103, a detecting section 104, a calculating section 105, a first deciding section 106, and a second deciding section 107.

The image producing section 101 produces an image of the subject 5 based on the image data obtained from the sensor section 19.

The display control section 102 controls the gantry display section 18 so that an image and/or necessary information etc. are displayed in the gantry display section 18.

The contour-data generating section 103 generates contour data representing a contour of the subject 5 based on the distance data obtained from the sensor section 19. A method of generating the contour data will be discussed later.

The detecting section 104 detects a body part to be imaged of the subject 5 based on the distance data obtained from the sensor section 19.

The calculating section 105 calculates an amount $\Delta y_c$ of movement of the cradle 41 in the y-direction and an amount $\Delta z_c$ of movement of the cradle 41 in the z-direction required to carry the body part to be imaged of the subject 5 to a prespecified position within the bore B of the gantry 2. A method of the calculation will be discussed later.

The first deciding section 106 decides whether or not there is a risk for the subject 5 to come into contact with the gantry 2 based on a limit surface representing a limit of a range up to which the subject 5 can come close to the gantry 2. Now the limit surface will be described below.

Figure 5:
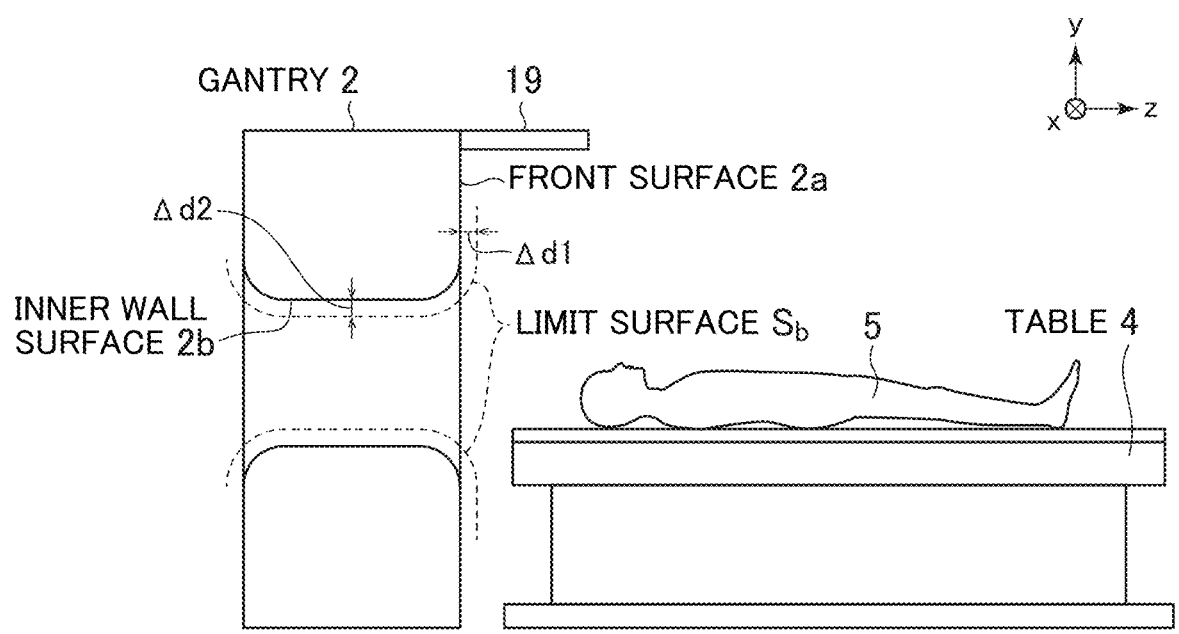
FIG. 5 is an explanatory diagram for a limit surface.

FIG. 5 is an explanatory diagram for the limit surface.

A limit surface Sb represents a limit of the range up to which the subject 5 can come close to the gantry 2. Data of the limit surface Sb is stored in, for example, the storage device 63. In the present embodiment, the limit surface Sb is defined to represent a limit of a range up to which the subject 5 can come close to a front surface 2a and an inner wall surface 2b of the gantry 2. The limit surface Sb may be defined so that, for example, it covers the front surface 2a of the gantry 2 at a position away from the front surface 2a of the gantry 2 by a distance $\Delta d1$ and also it covers the inner wall surface 2b of the gantry 2 at a position away from the inner wall surface 2b of the gantry 2 by a distance $\Delta d2$. The distances $\Delta d1$ and $\Delta d2$ may be set so that $\Delta d1=\Delta d2$ or $\Delta d1\neq\Delta d2$. $\Delta d1$ and $\Delta d2$ may be set at a value of a few centimeters, for example. The value of $\Delta d1$ may be identical all over the front surface 2a of the gantry 2, or it may be set at different values by hypothetically dividing the front surface 2a of the gantry 2 into a plurality of facets and setting different values on a facet-by-facet basis. Likewise, the value of $\Delta d2$ may be identical all over the inner wall surface 2b of the gantry 2, or it may be set at different values by hypothetically dividing the inner wall surface 2b of the gantry 2 into a plurality of facets and setting different values on a facet-by-facet basis.

The first deciding section 106 decides that there is a risk for the subject 5 to come into contact with the gantry 2 in the case that at least part of the subject 5 comes close to the gantry 2 beyond the limit surface Sb. A particular method for the decision method will be discussed later.

The second deciding section 107 decides whether or not the cradle 41 has moved by the amounts $\Delta y_c$ and $\Delta z_c$ of movement, which will be discussed later.

The image producing section 101 constitutes an example of the image producing means, the contour-data generating section 103 constitutes an example of the contour-data generating means, and the first deciding section 106 constitutes an example of the deciding means.

Programs for implementing these functional blocks may be stored in the storage device 63 in the operation console 6, or stored in at least one of a storage section in the gantry 2 and that in the table 4. The gantry 2, table 4, and operation console 6 serve as computers for executing the programs stored in the storage device or storage section(s), and the computers function as respective functional blocks by executing the programs stored in the storage device or storage section(s). It is possible to store at least part of the programs into a storage section or a storage medium 90 (see FIG. 2) externally connected with the operation console 6. Details of the functions shown in FIG. 4 will be described later in explaining the processing flow in the X-ray CT apparatus.

In the present embodiment, the CT apparatus 1 comprises a contact avoidance apparatus for avoiding contact of the subject 5 with the gantry 2 while the subject 5 is being carried toward the bore B of the gantry 2. Therefore, the subject 5 can be safely carried toward the bore B of the gantry 2. Now the flow of carrying the subject 5 toward the bore B of the gantry 2 will be described referring to FIG. 6.

Figure 6:
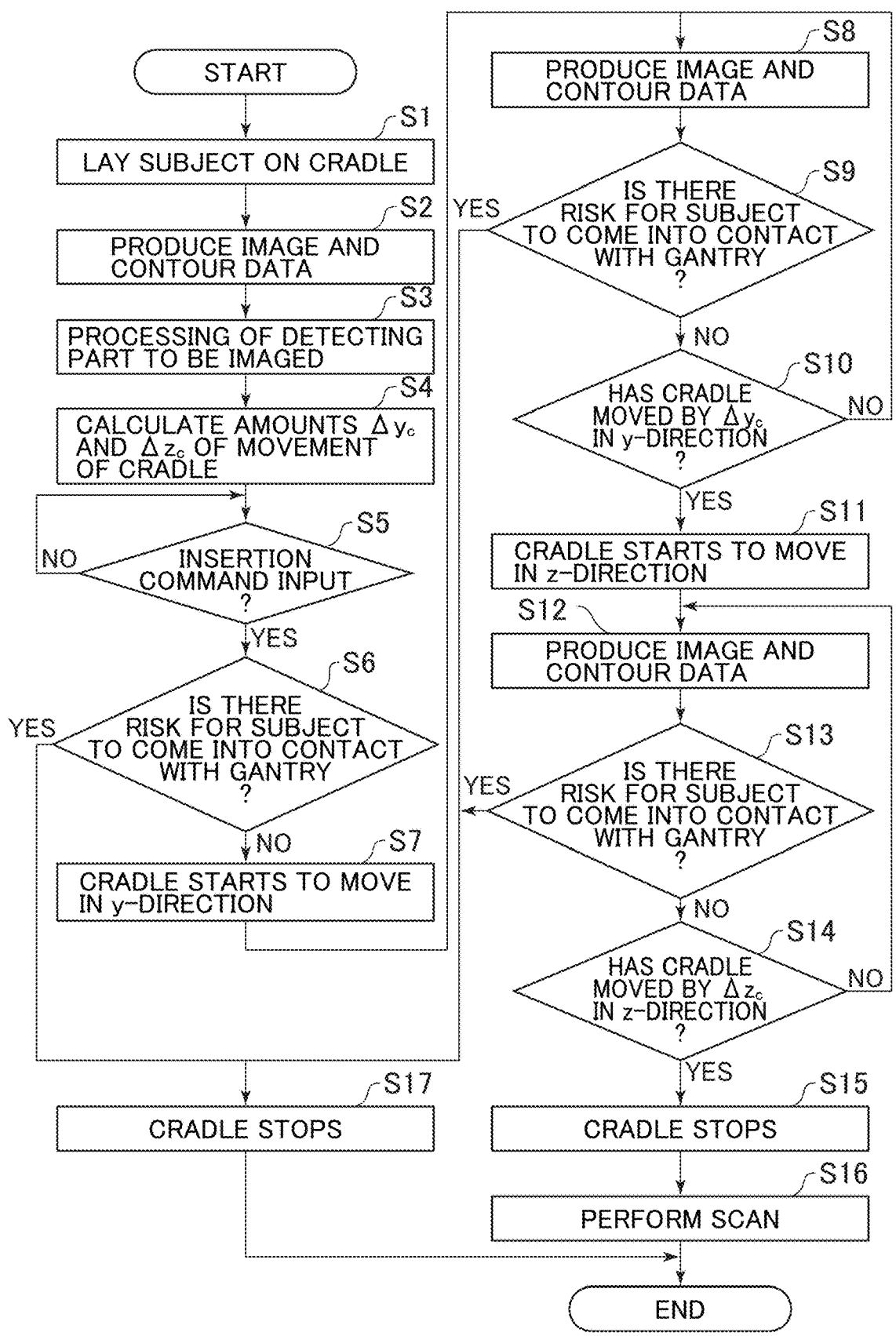
FIG. 6 is a diagram showing an exemplary operation flow in the first embodiment.

FIG. 6 is a diagram showing an exemplary operation flow in the first embodiment.

Figure 7:
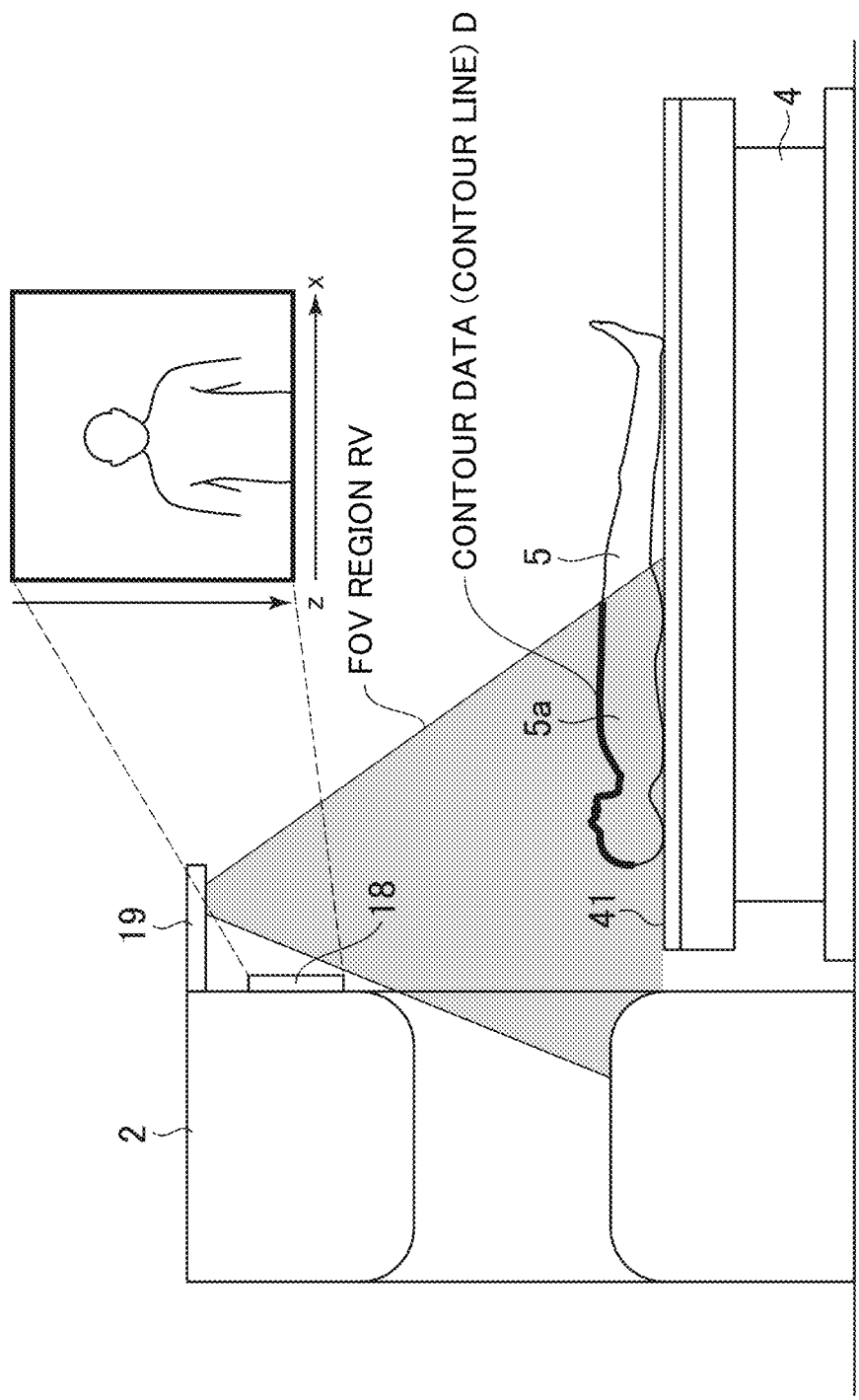
FIG. 7 is a diagram showing a condition in which a subject 5 is laid on a cradle 41.

At Step S1, the radiographer lays the subject 5 on the cradle 41 of the table 4 (see FIG. 7). The radiographer also sets scan conditions (a body part to be imaged, for example) for the subject 5. While the body part to be imaged is considered as a head part here, it is not limited thereto and may be any other body part, such as a shoulder part, a chest part, an abdominal part, or a leg part. After the subject 5 is laid on the cradle 41 as shown in FIG. 7, the process goes to Step S2.

At Step S2, the image producing section 101 (see FIG. 4) produces an image of the subject 5 based on image data obtained from the sensor section 19. The display control section 102 (see FIG. 4) controls the gantry display section 18 so that the image produced by the image producing section 101 is displayed in the gantry display section 18. FIG. 7 schematically shows the image displayed in the gantry display section 18.

Figure 8:
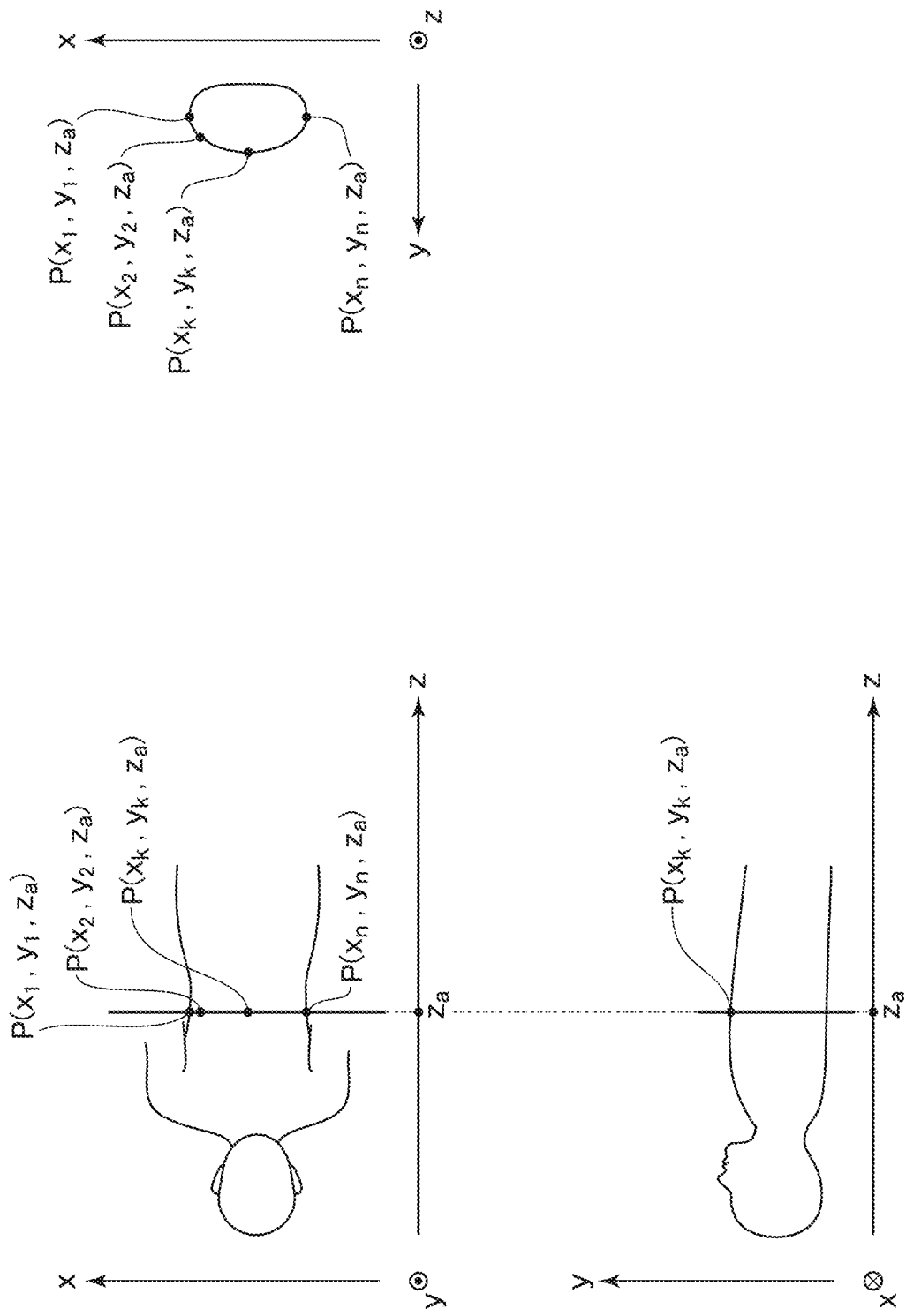
FIG. 8 is an explanatory diagram for a method of generating contour data.

Moreover, at Step S2, the contour-data generating section 103 (see FIG. 4) generates contour data representing a contour of the subject 5 in the z-direction falling within the field-of-view region RV of the sensor section 19 based on distance data obtained by the sensor section 19. FIG. 8 is an explanatory diagram for an exemplary method of generating the contour data.

In the present embodiment, the contour data is determined based on information on positions at points on the surface of the subject 5. In determining the value of the contour data at $z=z_a$, for example, a maximum of y-coordinates $y_1$, $y_2, \ldots, y_k, \ldots, y_n$ of points $P(x_1, y_1, z_a)$, $P(x_2, y_2, z_a), \ldots, P(x_k, y_k, z_a), \ldots, P(x_n, y_n, z_a)$ at $z=z_a$ on the body surface of the subject 5 can be set for the value of the contour data at $z=z_a$. It should be noted that the value of the contour data is not limited to the maximum of $y_1, y_2, \ldots, y_k, \ldots, y_n$, and it may be an average of $y_1, y_2, \ldots, y_k, \ldots, y_n$, for example.

The contour data D generated is schematically shown in FIG. 7. In the present embodiment, the contour data D is generated as a contour line representing the contour of the subject 5 in the z-direction. After generating the contour data D, the process goes to Step S3.

Figure 9:
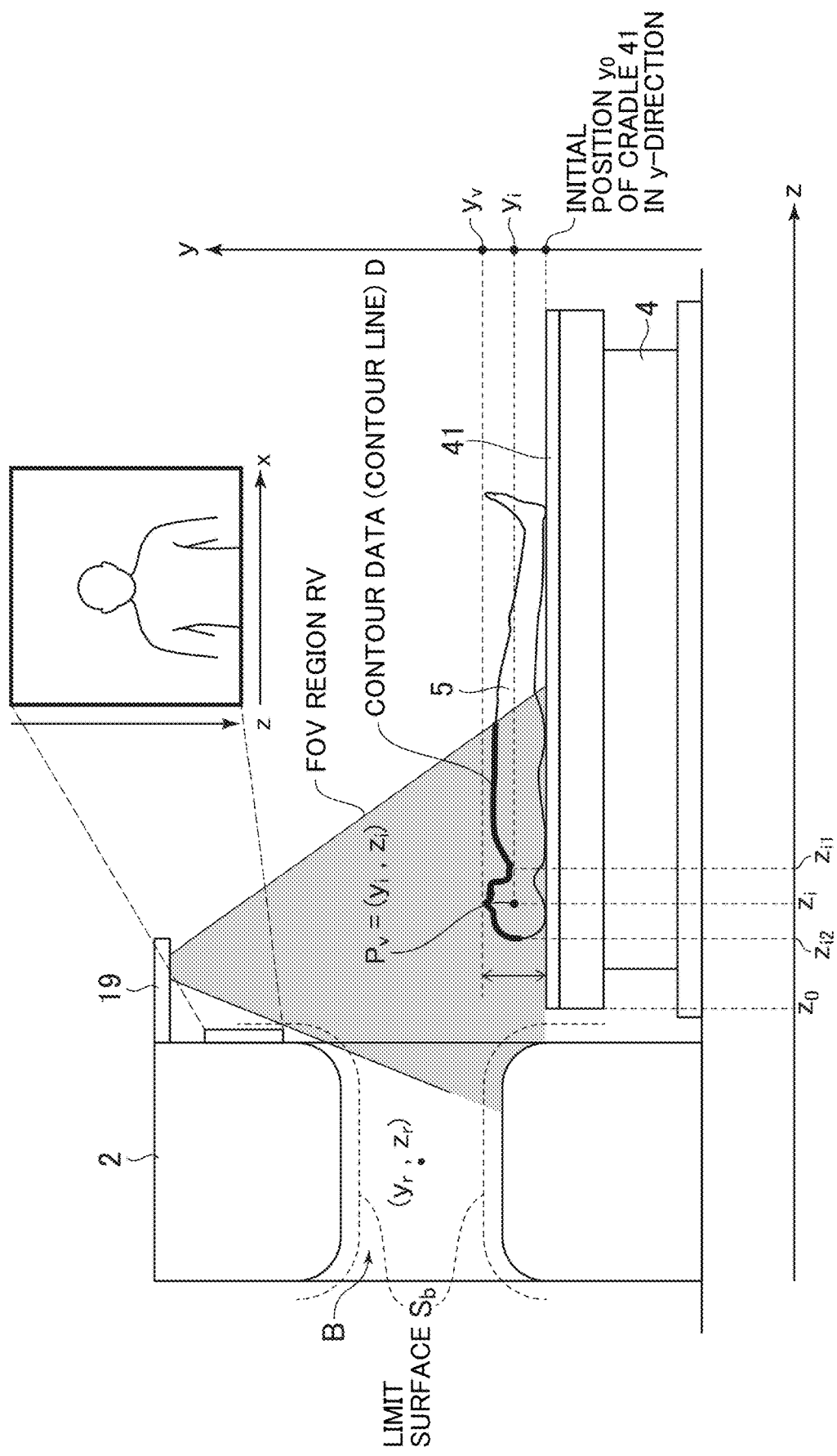
FIG. 9 is a diagram showing a position Pv of a head that is detected.

At Step S3, the detecting section 104 (see FIG. 6) generates, based on the distance data, three-dimensional (3D) data representing the 3D shape of the body surface of the subject 5 in the field-of-view region RV, and executes processing for detecting the body part to be imaged from the 3D data. Since the head part is set for the body part to be imaged here, the detecting section 104 executes processing for detecting the head part of the subject 5. An exemplary method of detecting the body part to be imaged comprises preparing beforehand templates representing the standard shapes of body parts to be imaged, such as the head part, shoulder part, chest part, abdominal part, and leg part, and performing matching of the 3D data with each template to detect the body part to be imaged. Referring to FIG. 7, the head part, which is the body part to be imaged, falls within the field-of-view region RV. Thus, the detecting section 104 can detect the head part based on the distance data. FIG. 9 shows a position Pv of the detected head part as $Pv=(y_i, z_i)$. The position $y_i$ of the head part in the y-direction here is calculated as a mid-position between a maximum $y_v$ of the position on the surface of the head part of the subject 5 in the y-direction, and a position $y_0$ of the cradle 41 in the y-direction, that is, $y=(y_0+y_v)/2$. The position $z_i$ of the head part in the z-direction is calculated as a mid-position in a range $z_{i1}$ to $z_{i2}$ of the head part of the subject 5 in the z-direction, that is, $z=(z_{i1}+z_{i2})/2$. However, any position offset from the mid-positions described above may be calculated as the position of the head part.

After detecting the head part, the process goes to Step S4.

Figure 10:
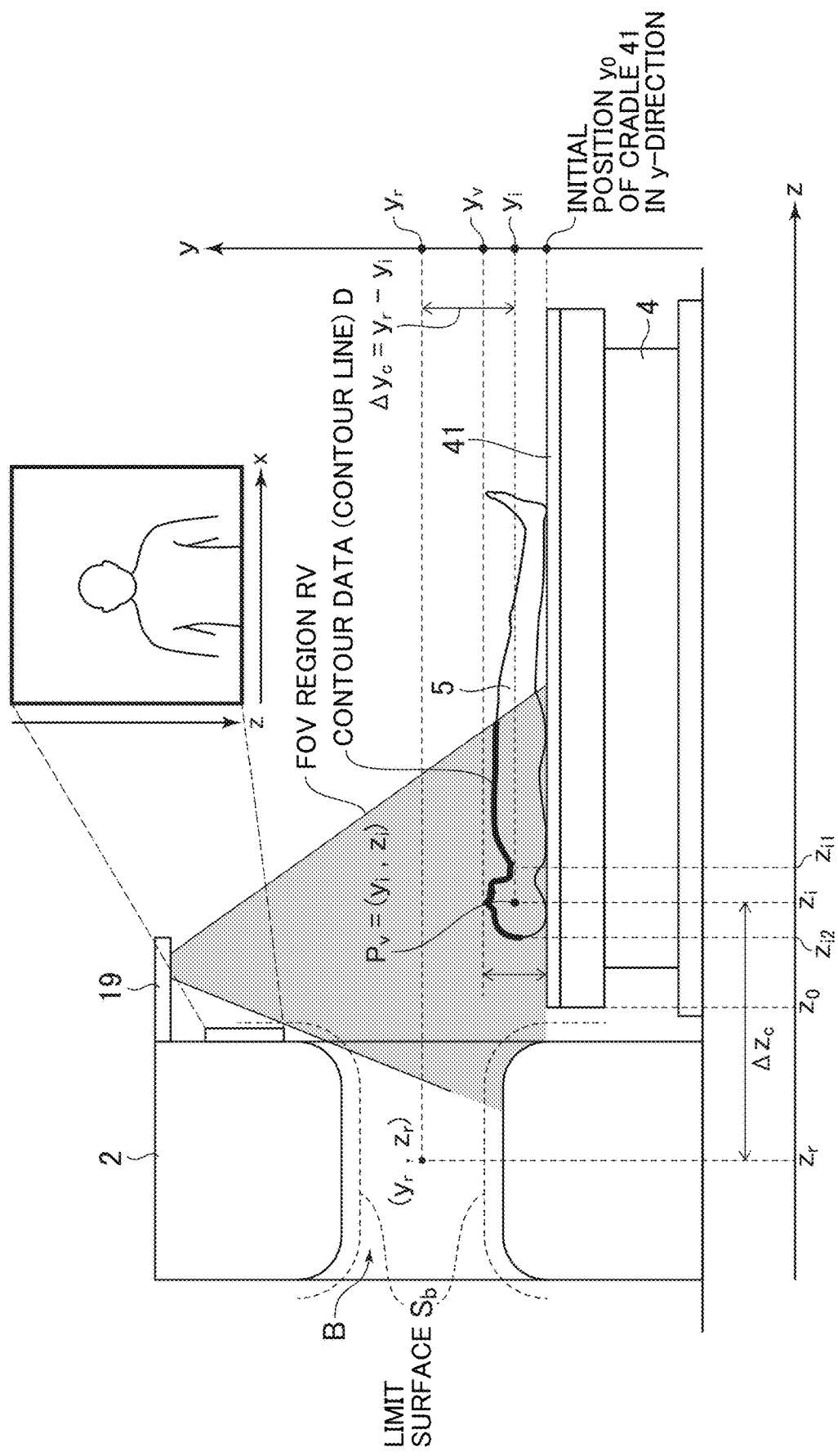
FIG. 10 is an explanatory diagram for an exemplary method of calculating amounts $\Delta y_c$ and $\Delta z_c$ of movement of the cradle 41.

At Step S4, the calculating section 105 (see FIG. 4) calculates amounts $\Delta y_c$ and $\Delta z_c$ of movement of the cradle 41 required to position the head part of the subject 5 at a prespecified position $(y_r, z_r)$ in the bore B of the gantry 2 (see FIG. 10).

FIG. 10 is an explanatory diagram for an exemplary method of calculating the amounts $\Delta y_c$ and $\Delta z_c$ of movement of the cradle 41.

$\Delta y_c$ is the amount of movement of the cradle 41 in the y-direction required to position the head part of the subject 5 at the prespecified position $y_r$ in the bore B of the gantry 2 in the y-direction. On the other hand, $\Delta z_c$ is the amount of movement of the cradle 41 in the z-direction required to position the head part of the subject 5 at the prespecified position $z_r$ in the bore B of the gantry 2 in the z-direction. Since the position of the body part to be imaged in the y-direction is $y_i$ here, the calculating section 105 calculates $\Delta y_c = y_r - y_i$. Similarly, since the position of the body part to be imaged in the z-direction is $z_i$, the calculating section 105 calculates $\Delta z_c = z_r - z_i$. After calculating the amounts $\Delta y_c$ and $\Delta z_c$ of movement, the process goes to Step S5.

At Step S5, whether or not the radiographer has input a command to carry the subject 5 into the bore B of the gantry 2 is decided. In the case that the command of carrying is input, the process goes to Step S6. On the other hand, in the case that the command of carrying is not input, the process waits until the command of carrying is input.

Once the radiographer has input the command to carry the subject 5 into the bore B of the gantry 2 via the input device, the process goes to Step S6.

At Step S6, the first deciding section 106 decides whether or not there is a risk for the subject 5 to come into contact with the gantry 2 based on the contour data (contour line) D. Now a method of the decision will be particularly described below.

The first deciding section 106 reads out, from the storage section, the limit surface Sb (see FIG. 5) representing the limit of the range up to which the subject 5 can come close to the gantry 2. The first deciding section 106 then decides whether or not the contour line D that the contour data represents is tangent to or intersects the limit surface Sb. In the case that the contour line D is tangent to or intersects the limit surface Sb, the first deciding section 106 decides that there is a risk for the subject 5 to come into contact with the gantry 2. In this case, the process goes to Step S17, where the cradle (table) stops and the flow is terminated. On the other hand, in the case that the contour line D that the contour data represents is not tangent to or does not intersect the limit surface Sb, the first deciding section 106 decides that there is no risk for the subject 5 to come into contact with the gantry 2, and the process goes to Step S7.

In FIG. 10, the contour line D lies farther away from the gantry 2 with respect to the limit surface Sb. Therefore, the first deciding section 106 decides that the contour line D is not tangent to or does not intersect the limit surface Sb. In this case, the first deciding section 106 decides that there is no risk for the subject 5 to come into contact with the gantry 2, and accordingly, the process goes to Step S7.

Figure 11:
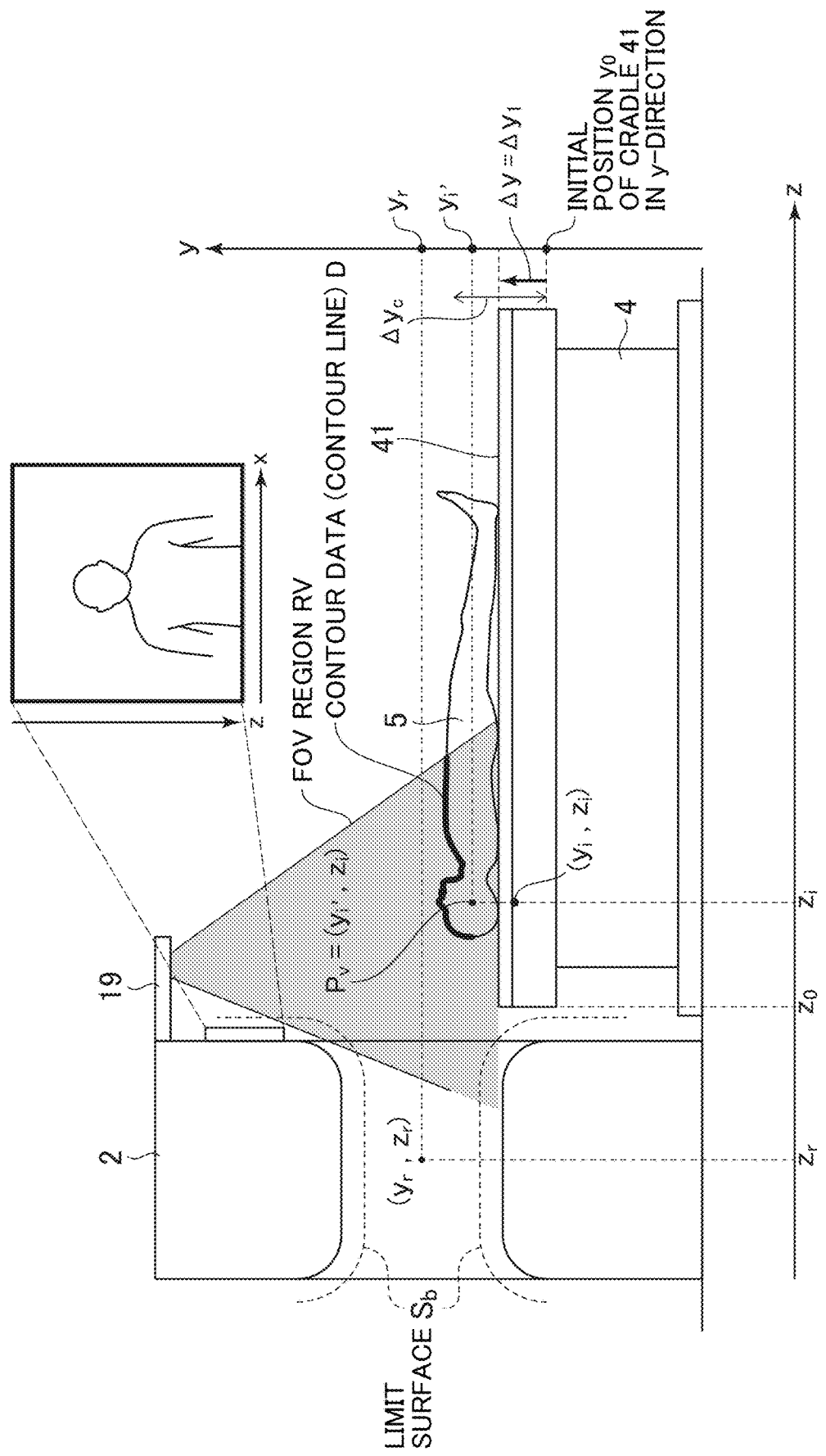
FIG. 11 is a diagram showing a condition in which the cradle 41 has been moved by $\Delta y = \Delta y_1$ in a y-direction.

At Step S7, the control section 30 controls the table 4 so that the cradle 41 starts moving in the y-direction. Thus, movement of the cradle 41 in the y-direction is started. FIG. 11 shows a condition in which the cradle 41 has moved by $\Delta y = \Delta y_1$ in the y-direction.

At Step S8, the image producing section 101 produces an image of the subject 5 based on image data obtained from the sensor section 19. The display control section 102 controls the gantry display section 18 so that the image produced by the image producing section 101 is displayed in the gantry display section 18. In FIG. 11 is schematically shown the image at a time point when the cradle 41 has moved by $\Delta y = \Delta y_1$ in the y-direction.

Moreover, the contour-data generating section 103 generates contour data at the time point when the cradle 41 has moved by $\Delta y = \Delta y_1$ in the y-direction based on distance data obtained from the sensor section 19.

At Step S9, the first deciding section 106 decides whether or not there is a risk for the subject 5 to come into contact with the gantry 2 based on the contour line D. In the case that the contour line D is tangent to or intersects the limit surface Sb, the first deciding section 106 decides that there is a risk for the subject 5 to come into contact with the gantry 2. In this case, the process goes to Step S17, where the cradle (table) stops and the flow is terminated. In FIG. 11, the contour line D lies farther away from the gantry 2 with respect to the limit surface Sb. Therefore, the first deciding section 106 decides that the contour line D is not tangent to or does not intersect the limit surface Sb, so that it is decided that there is no risk for the subject 5 to come into contact with the gantry 2, and the process goes to Step S10.

At Step S10, the second deciding section 107 (see FIG. 4) decides whether or not the cradle 41 has moved by $\Delta y_c$ in the y-direction. As shown in FIG. 11, the cradle 41 has moved only by $\Delta y = \Delta y_1$ ($<\Delta y_c$) yet. Accordingly, the process goes back to Step S8.

At Step S8, while the cradle 41 is moving in the y-direction, the contour-data generating section 103 generates the contour line D and updates the contour data (contour line) D to the latest data each time the position of the cradle 41 in the y-direction is changed. On the other hand, at Step S9, each time the contour data (contour line) D is updated, the first deciding section 106 decides whether or not there is a risk for the subject 5 to come into contact with the gantry 2 based on the contour line D and limit surface Sb, and in the case that there is no risk for the subject 5 to come into contact with the gantry 2, the second deciding section 107 decides whether or not the cradle 41 has moved by $\Delta y_c$ at Step S10.

Therefore, in the case that it is decided that there is no risk for the subject 5 to come into contact with the gantry at Step S9, and at the same time it is decided that the cradle 41 has not moved by $\Delta y_c$ in the y-direction at Step S10, a loop of Steps S8, S9, and S10 is repetitively executed.

Figure 12:
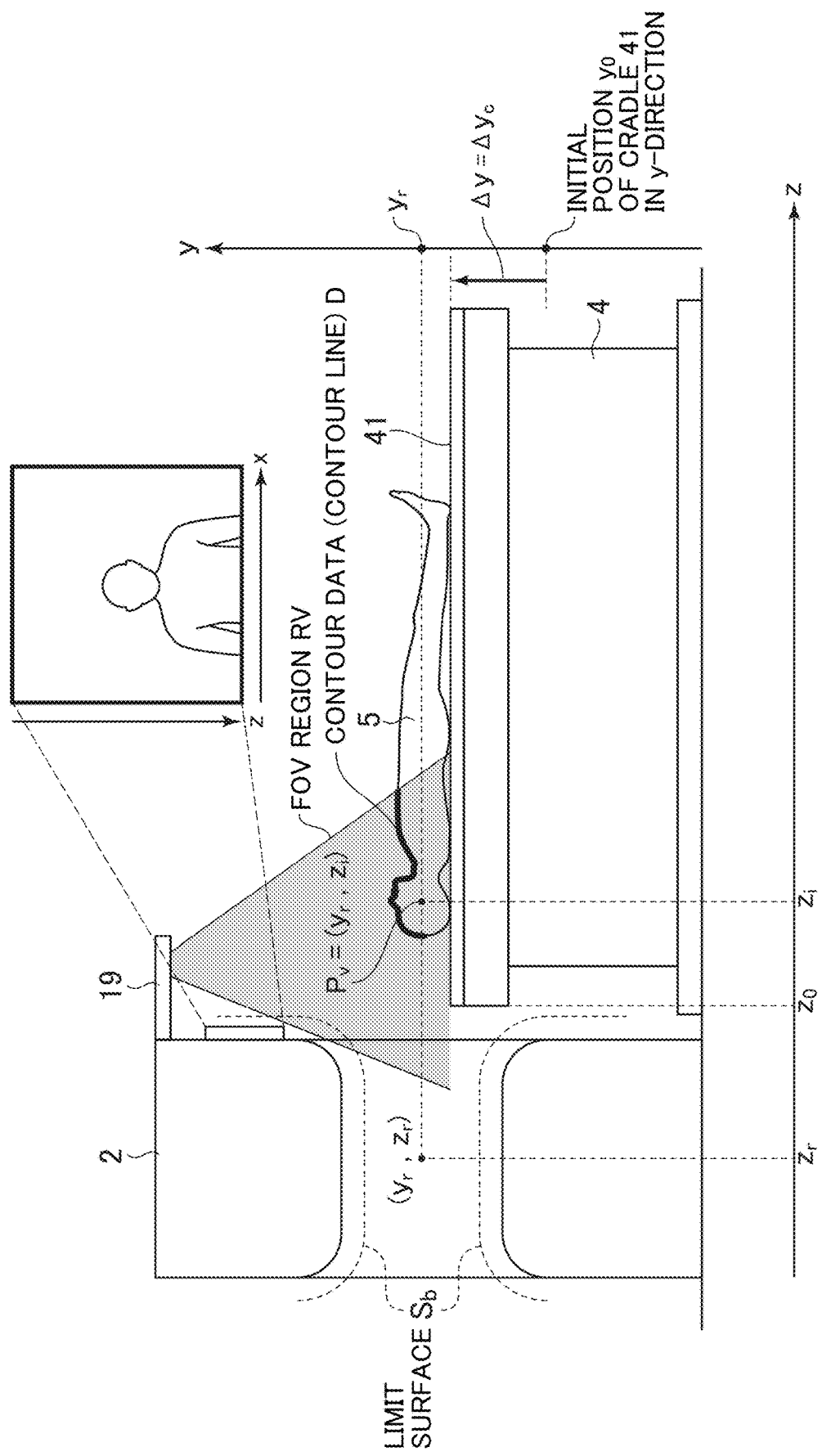
FIG. 12 is a diagram showing a condition in which a table 4 has been moved by $\Delta y = \Delta y_c$ in the y-direction.

FIG. 12 is a diagram showing a condition in which the cradle 41 has moved by $\Delta y = \Delta y_c$ in the y-direction.

Once the cradle 41 has moved by $\Delta y = \Delta y_c$, the position Pv of the head part reaches $Pv=(y_r, z_i)$. In this case, at Step S10, the second deciding section 107 decides that the cradle 41 has moved by $\Delta y = \Delta y_c$. Accordingly, the process goes to Step S11.

Figure 13:
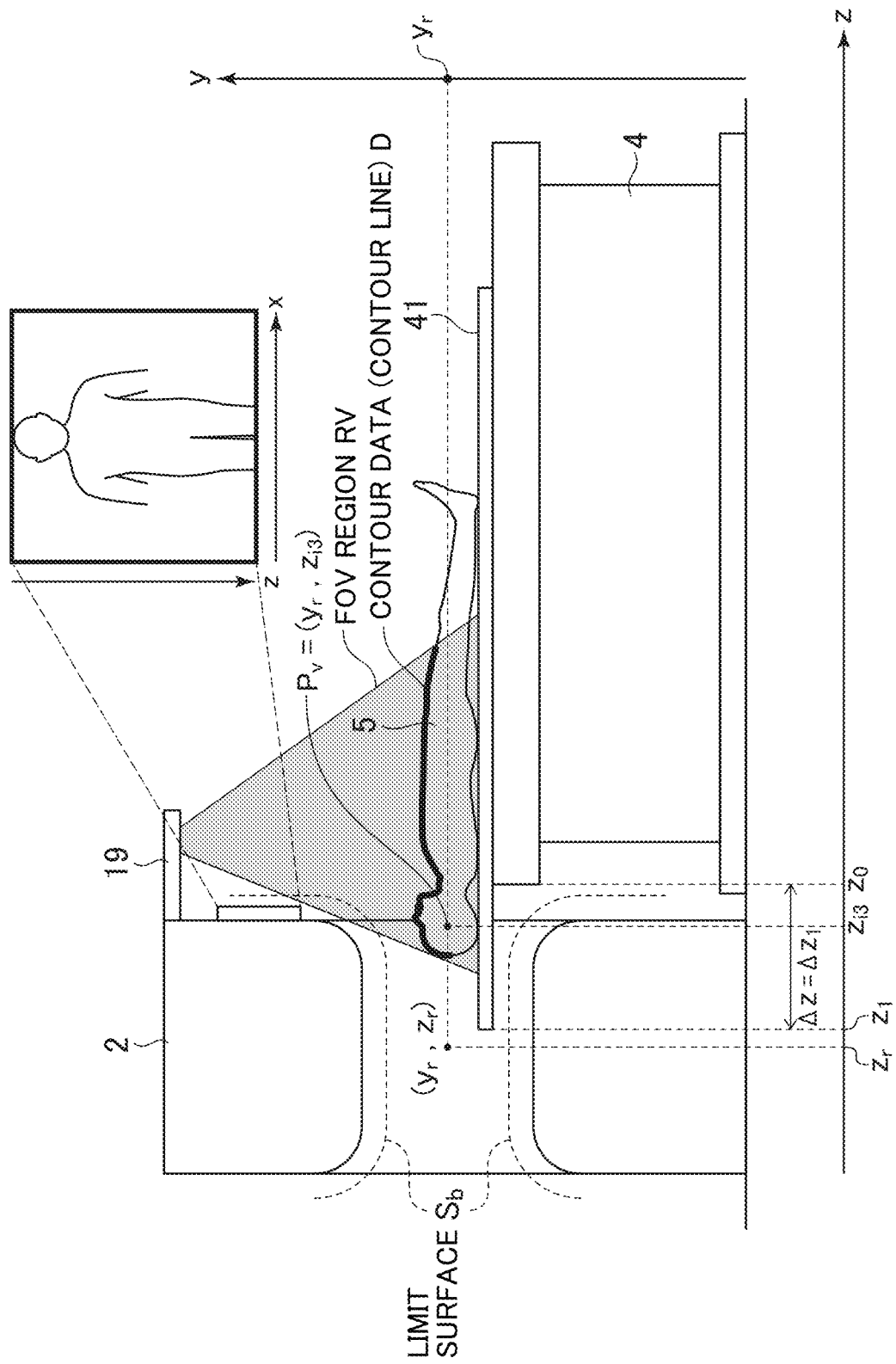
FIG. 13 is a diagram showing the cradle 41 having reached $z = z_1$.

At Step S11, the movement of the cradle 41 in the y-direction stops, and movement of the cradle 41 in the z-direction is started. FIG. 13 is a diagram showing a condition in which the cradle 41 has moved from $z=z_0$ to $z=z_1$ (the cradle 41 has moved by $\Delta z=\Delta z_1$).

At Step S12, the image producing section 101 produces an image of the subject 5 based on image data obtained from the sensor section 19. The display control section 102 controls the gantry display section 18 so that the image produced by the image producing section 101 is displayed in the gantry display section 18. In FIG. 13 is schematically shown the image at a time point when the cradle 41 has moved by $\Delta z=\Delta z_1$ in the z-direction.

Moreover, the contour-data generating section 103 generates contour data at the time point when the cradle 41 has moved by $\Delta z=\Delta z_1$ in the z-direction based on distance data obtained from the sensor section 19.

At Step S13, the first deciding section 106 decides whether or not there is a risk for the subject 5 to come into contact with the gantry 2 based on the contour line D. In the case that the contour line D is tangent to or intersects the limit surface Sb, the first deciding section 106 decides that there is a risk for the subject 5 to come into contact with the gantry 2. In this case, the process goes to Step S17, where the cradle (table) stops and the flow is terminated. In FIG. 13, the contour line D lies farther away from the gantry 2 with respect to the limit surface Sb. Therefore, the first deciding section 106 decides that the contour line D is not tangent to or does not intersect the limit surface Sb, so that it is decided that there is no risk for the subject 5 to come into contact with the gantry 2, and the process goes to Step S14.

At Step S14, the second deciding section 107 decides whether or not the cradle 41 has moved by $\Delta z_c$ in the z-direction. Here, the cradle 41 has moved only by $\Delta z=\Delta z_1$ ($<\Delta z_c$) yet. Accordingly, the process goes back to Step S12.

At Step S12, while the cradle 41 is moving in the z-direction, the contour-data generating section 103 generates the contour line D and updates the contour data (contour line) D to the latest data each time the position of the cradle 41 in the z-direction is changed. On the other hand, at Step S13, each time the contour data (contour line) D is updated, the first deciding section 106 decides whether or not there is a risk for the subject 5 to come into contact with the gantry 2 based on the contour line D and limit surface Sb, and in the case that there is no risk for the subject 5 to come into contact with the gantry 2, the second deciding section 107 decides whether or not the cradle 41 has moved by $\Delta z_c$ at Step S14.

Therefore, in the case that it is decided that there is no risk for the subject 5 to come into contact with the gantry at Step S13, and at the same time it is decided that the cradle 41 has not moved by $\Delta z_c$ in the z-direction at Step S14, a loop of Steps S12, S13, and S14 is repetitively executed.

Figure 14:
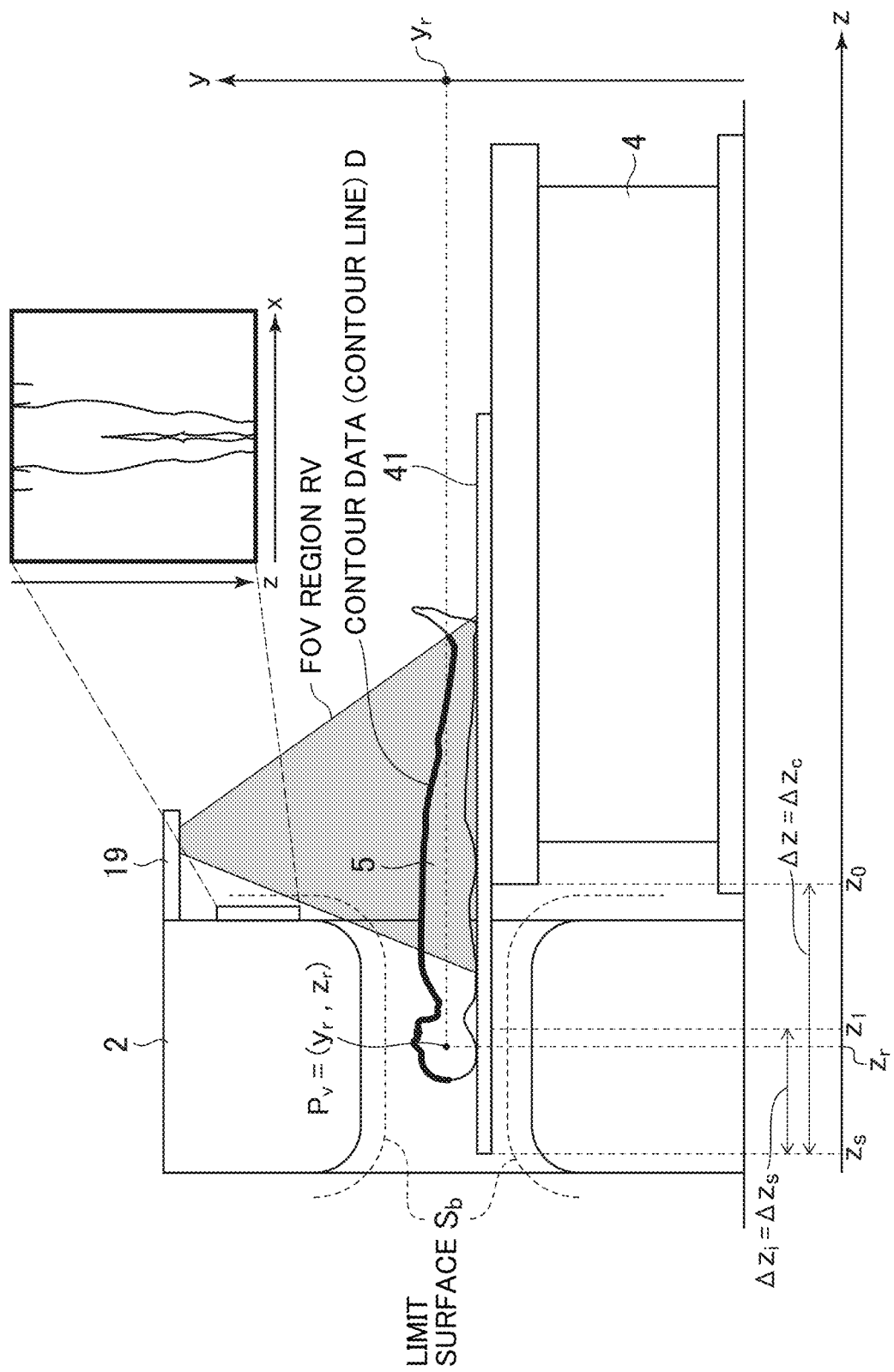
FIG. 14 is a diagram showing a condition in which the cradle 41 has moved by $\Delta z = \Delta z_c$ in a z-direction.

FIG. 14 is a diagram showing a condition in which the cradle 41 has moved by $\Delta z=\Delta z_c$ in the z-direction.

At a time point when the cradle 41 has reached $z=z_1$ (see FIG. 13), the head part of the subject 5 falls within the field-of-view region RV of the sensor section 19. However, when the cradle 41 further moves into the gantry 2 beyond $z=z_1$, the head part of the subject 5 gradually falls outside the field-of-view region RV, as shown in FIG. 14. Accordingly, in the present embodiment, when the cradle 41 further moves into the gantry beyond $z=z_1$, the contour-data generating section 103 shifts the positions of points in the contour data (contour line) D in the z-direction when the cradle 41 has reached $z=z_1$ (see FIG. 13) by an amount $\Delta z_i$ of movement from $z=z_1$, and generates contour data (contour line) D after the shift as the contour data (contour line) D of the subject 5 in a range $z_1 < z \leq z_s$. When the cradle 41 has reached $z=z_s$, the amount $\Delta z_i$ of movement is $\Delta z_i = \Delta z_s$, so that the contour data (contour line) D when the cradle 41 has reached $z=z_s$ is derived by shifting the position in the z-direction by $\Delta z_s$ relative to the contour data (contour line) D when the cradle 41 has reached $z=z_1$ (see FIG. 13).

Once the cradle 41 has moved by $\Delta z=\Delta z_c$, the position Pv of the head part reaches $Pv=(y_r, z_r)$. In this case, at Step S14, the second deciding section 107 decides that the cradle 41 has moved by $\Delta z=\Delta z_c$. Accordingly, the process goes to Step S15.

At Step S15, the control section 30 controls the cradle 41 to stop. The process then goes to Step S16, where a scan is performed and the flow is terminated.

As described referring to FIGS. 7 to 14, in the period of time from when the cradle 41 starts moving until when the head part of the subject 5 reaches the prespecified position $(y_r, z_r)$, the contour line D is not tangent to or does not intersect the limit surface Sb. Therefore, it can be seen that there occurs no risk for the subject 5 to come into contact with the gantry 2 in the period of time from when the cradle 41 starts moving until when the head part of the subject 5 reaches the prespecified position $(y_r, z_r)$.

Now an exemplary case in which there is a risk, on the other hand, for the subject 5 to come into contact with the gantry 2 during movement of the cradle 41 will be described referring to FIG. 15.

Figure 15:
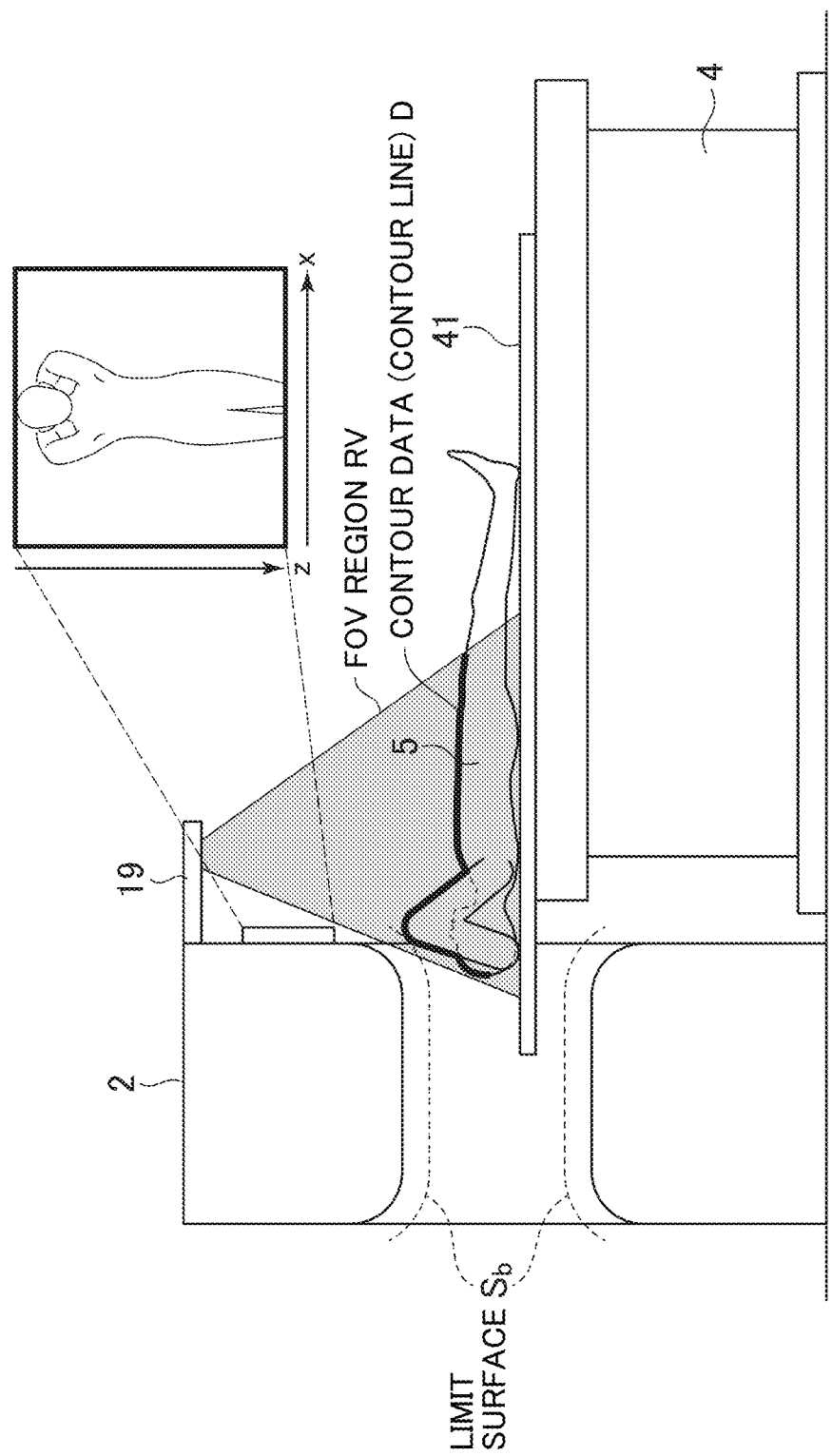
FIG. 15 is a diagram showing a condition in which the subject 5 brings up his/her arms.

In FIG. 15, a case in which the body part to be imaged is the chest part is shown, wherein is shown a condition in which the subject 5 raises his/her arms to prevent the arm part from falling within an imaged range. FIG. 15 shows a case in which the contour line D is tangent to the limit surface Sb in the course of the cradle 41 moving in the z-direction.

In this case, at Step S13, the first deciding section 106 decides that the contour line D is tangent to the limit surface Sb. Therefore, the first deciding section 106 decides that there is a risk for the subject 5 to come into contact with the gantry 2 when the cradle 41 continues to move. Accordingly, the process goes to Step S17.

At Step S17, the control section 30 controls the cradle 41 to stop, and the flow is terminated. Thus, a risk for the subject 5 to come into contact with the cradle 41 can be avoided.

As described above, in the present embodiment, it is decided whether or not there is a risk for the subject 5 to come into contact with the gantry 2 in the period of time from when the cradle 41 starts moving in the y-direction until when the head part of the subject 5 reaches the prespecified position $(y_r, z_r)$. In the case that there is no risk for the subject 5 to come into contact with the gantry 2, the head part of the subject 5 reaches the prespecified position $(y_r, z_r)$. Thus, the operator can start a scan.

On the other hand, in the case that the contour line D is tangent to or intersects the limit surface Sb (see FIG. 15) in the period of time from when the cradle 41 starts moving in the y-direction until when the head part of the subject 5 reaches the prespecified position $(y_r, z_r)$, it is decided that there is a risk for the subject 5 to come into contact with the gantry 2. In this case, the cradle 41 stops even when the head part of the subject 5 has not reached the prespecified position $(y_r, z_r)$. Thus, a risk for the subject 5 to come into contact with the gantry 2 can be avoided.

In the present embodiment, moreover, by deciding whether or not the contour data for the subject 5 is tangent to or intersects the limit surface Sb, contact of the subject 5 to the gantry 2 can be avoided, which eliminates the need for a sensor for detecting contact between the subject 5 and the gantry 2. Thus, manufacturing costs can also be reduced.

The first embodiment addresses a case of avoiding contact between the gantry 2 and the subject 5 by generating contour data for the subject 5 in the z-direction. In a second embodiment, a case of avoiding contact with the subject 5 by generating contour data for the subject 5 as viewed from directly above (contour data for the subject 5 in a zx-plane) will be described below.

The operation flow in the second embodiment will be described referring to the flow in FIG. 6, as with the first embodiment.

At Step S1, the subject 5 is laid on the cradle 41, and then, the process goes to Step S2.

At Step S2, the image producing section 101 produces an image of the subject 5 based on image data obtained from the sensor section 19. The display control section 102 controls the gantry display section 18 so that the image produced by the image producing section 101 is displayed in the gantry display section 18.

Figure 16:
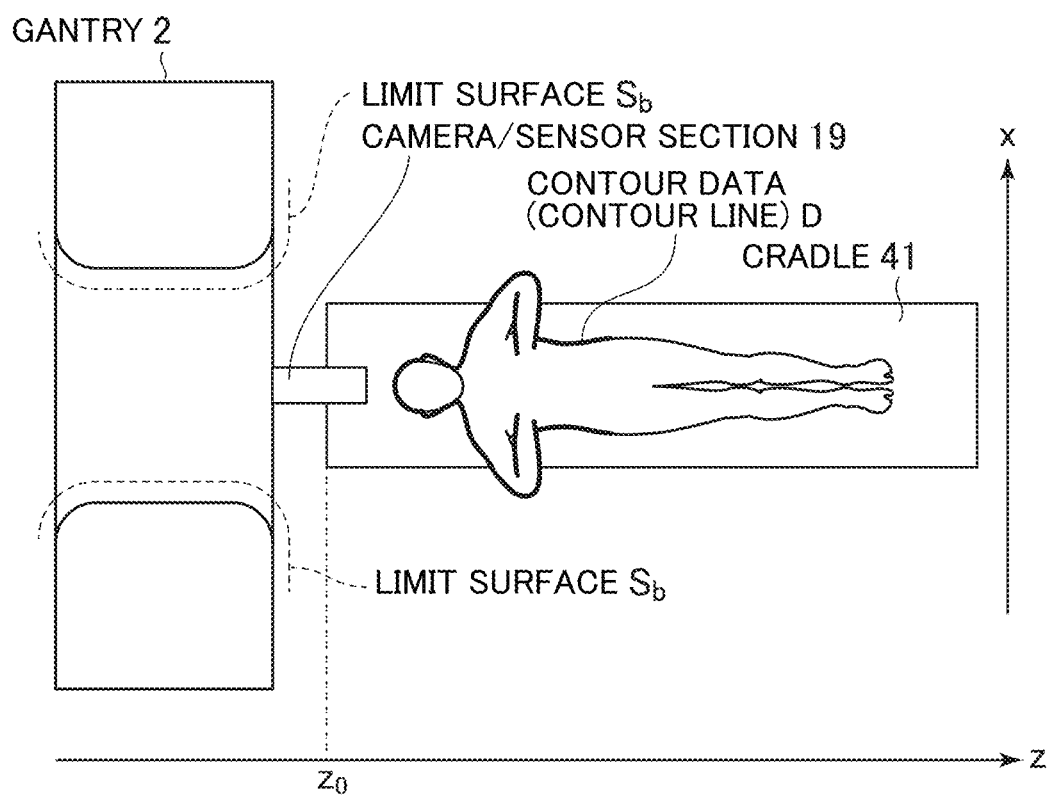
FIG. 16 is an explanatory diagram for a method of deciding whether there is a risk for the subject 5 to come into contact with a gantry 2.

Moreover, at Step S2, the contour-data generating section 103 generates contour data D representing a contour of the subject 5 in the zx-plane falling within the field-of-view region RV of the sensor section 19 based on distance data obtained from the sensor section 19. FIG. 16 schematically shows the contour data D in the zx-plane by a bold curved line. After generating the contour data D, the process goes to Step S3.

Steps S3 to S5 are identical to those in the first embodiment, the explanation of which will be omitted. Once the radiographer has input the command to carry the subject 5 into the bore B of the gantry 2 via the input device at Step S5, the process goes to Step S6.

At Step S6, the first deciding section 106 decides whether or not there is a possibility for the subject 5 to come into contact with the gantry 2.

The first deciding section 106 decides whether or not the contour data (contour line) D is tangent to or intersects the limit surface Sb. In FIG. 16, the contour data (contour line) D lies away from the limit surface Sb. In this case, the contour line D is not tangent to or does not intersect the limit surface Sb, so that the first deciding section 106 decides that there is no risk for the subject 5 to come into contact with the gantry 2.

At Step S7, the control section 30 controls the table 4 so that the cradle 41 starts moving in the y-direction.

At Step S8, the image producing section 101 produces an image, and the contour-data generating section 103 generates contour data D for the subject 5 in the zx-plane. Then, the first deciding section 106 decides whether or not there is a risk for the subject 5 to come into contact with the gantry 2 based on the contour data D at Step S9, and the second deciding section 107 decides whether or not the cradle 41 has moved by $\Delta y_c$ in the y-direction at Step S10. While the cradle 41 is moving in the y-direction, the contour line D of the subject 5 is not tangent to or does not intersect the limit surface Sb. Therefore, while the cradle 41 is moving in the y-direction, the loop of Steps S8, S9, and S10 is repetitively executed.

Once the cradle 41 has moved by $\Delta y_c$ in the y-direction, the process goes to Step S11, where the cradle 41 starts moving in the z-direction.

At Step S12, the image producing section 101 produces an image, and the contour-data generating section 103 generates contour data D for the subject 5 in the zx-plane. Then, the first deciding section 106 decides whether or not there is a risk for the subject 5 to come into contact with the gantry 2 based on the contour data D at Step S13, and the second deciding section 107 decides whether or not the cradle 41 has moved by $\Delta z_c$ in the z-direction at Step S14.

Therefore, in the case that it is decided that there is no risk for the subject 5 to come into contact with the gantry at Step S13, and at the same time it is decided that the cradle 41 has not moved by $\Delta z_c$ in the z-direction at Step S14, the loop of Steps S12, S13, and S14 is repetitively executed.

Figure 17:
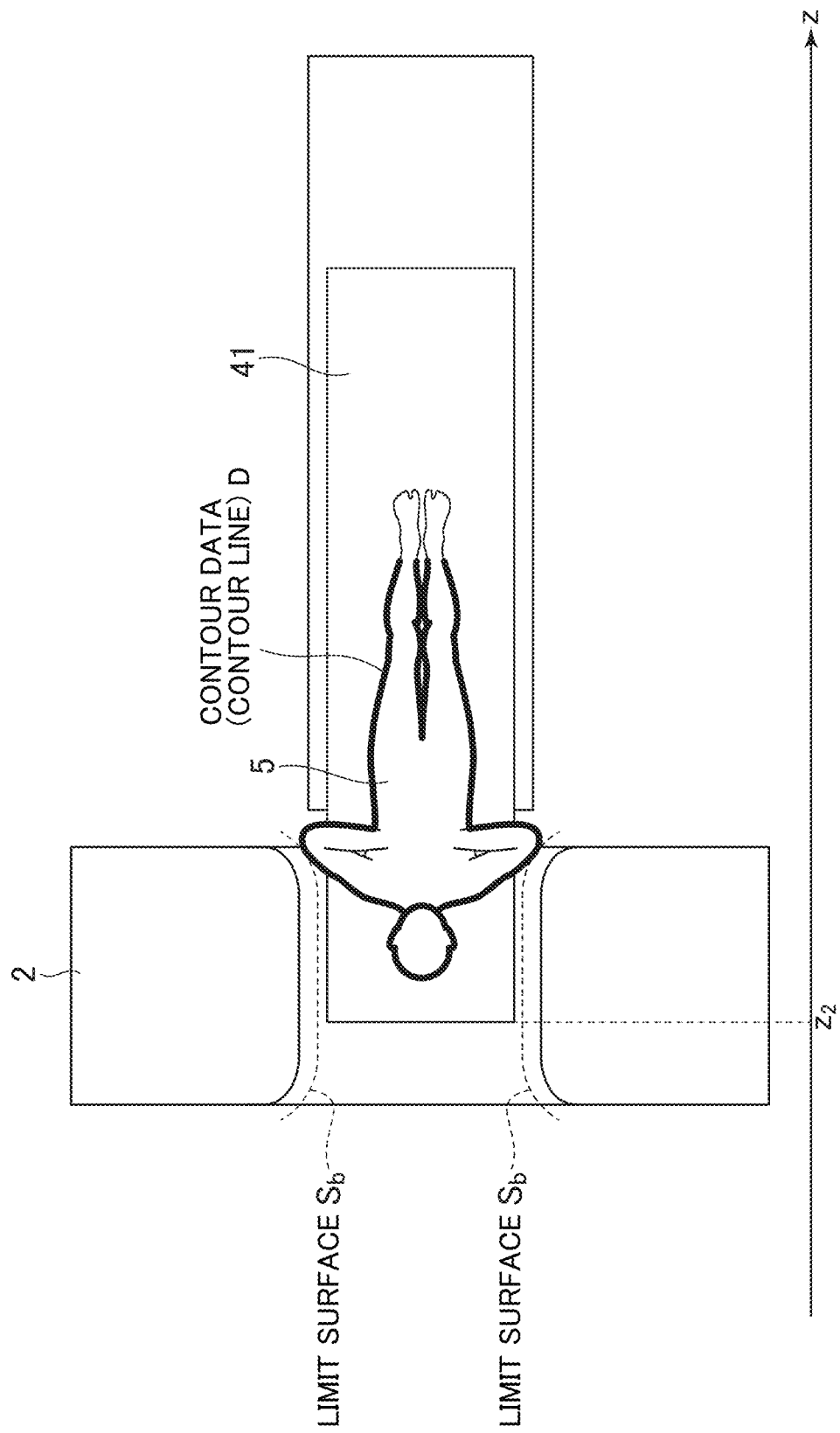
FIG. 17 is a diagram showing the cradle 41 having reached $z = z_2$.

FIG. 17 is a diagram showing the cradle 41 having reached $z=z_2$.

Referring to FIG. 17, the contour line D is tangent to the limit surface Sb at $z=z_2$. Therefore, the first deciding section 106 decides that there is a risk for the subject 5 to come into contact with the gantry 2 when the cradle 41 continues to move. In the case that there is a risk for the subject 5 to come into contact with the gantry 2, the process goes to Step S17.

At Step S17, the control section 30 controls the cradle 41 to stop. Once the cradle 41 has stopped, the flow is terminated.

In the second embodiment, again, in the case that contour line D is tangent to or intersects the limit surface Sb in the period of time from when the cradle 41 starts moving in the y-direction until when the head part of the subject 5 reaches the prespecified position in the gantry, it is decided that there is a risk for the subject 5 to come into contact with the gantry 2. In this case, the cradle 41 stops even when the head part of the subject 5 has not reached the prespecified position in the gantry. Thus, a risk for the subject 5 to come into contact with the gantry 2 can be avoided.

The first embodiment illustrates a case involving generating contour data representing the contour of the subject 5 in the z-direction, while the second embodiment illustrates a case involving generating contour data representing the contour of the subject 5 in the zx-plane. However, the contour data is not limited to these cases. For example, it may be contemplated to generate contour data as 3D data defined in an xyz-space, decide whether or not a contour plane that the contour data as 3D data represents is tangent to or intersects the limit surface Sb based on data from the sensor section 19, and thereby decide whether or not there is a risk for the subject 5 to come into contact with the gantry.

While described in the embodiments above is a case in which a risk for the subject 5 to come into contact with the gantry 2 during movement of the table 4 is avoided, the present invention is not limited to these embodiments. For example, in the case that the gantry 2 is provided with a tilt mechanism to allow it to be tilted with respect to the cradle 41, a risk for the subject 5 to come into contact with the gantry 2 may be avoided while the gantry 2 is moving (see FIG. 18).

FIG. 18 is an explanatory diagram for contact avoidance in the case that the gantry 2 is provided with a tilt mechanism.

FIG. 18 shows a condition in which the contour data is tangent to the limit surface Sb in the course of the gantry 2 tilting. In this case, the control section 30 controls the gantry 2 to stop its tilting action. Thus, contact of the subject 5 with the gantry 2 can be avoided.

In the first and second embodiments, each time the cradle 41 is moved, distance data is acquired from the sensor section 19 and new contour data D is generated. However, it may be contemplated, after generating the contour data D at Step S2, to calculate amounts $\Delta y_c$ and $\Delta z_c$ of movement of the cradle 41 at Step S4, and add $\Delta y$ ($0<\Delta y \leq \Delta y_c$) to the y-coordinates at each point in the contour data D generated at Step S2 and add $\Delta z$ ($0<\Delta z \leq \Delta z_c$) to the z-coordinates at each point in the contour data D before actually moving the cradle 41 (table 4), to thereby estimate the contour data D during movement of the cradle 41. This makes it possible to decide whether or not the subject 5 comes into contact with the gantry 2 without actually moving the cradle 41.

While in the first and second embodiments, the present invention is described focusing upon a CT apparatus, it may be applied to any medical apparatus (for example, an MRI apparatus) different from the CT apparatus.

The invention claimed is:

1. A contact avoidance apparatus for avoiding contact of a subject to be examined laid on a cradle of a table with a gantry, said apparatus comprising:
    a sensor section for acquiring distance data for determining a distance between said sensor section and at least part of said subject laid on said cradle;
    at least one processing unit; and
    a storage medium with a program stored therein, wherein when the at least one processing unit executes the program the program causes the at least one processing unit to:
        generate contour data representing a contour of said at least part of said subject;
        determine information on positions of points on a body surface of said at least part of said subject with respect to said cradle based on said distance data, and generates said contour data based on said information on positions;
        decide whether or not there is a risk for said subject to come into contact with said gantry while said gantry or said table is moving based on data representing a limit of a range up to which said subject can come close to said gantry and on said contour data; and
    wherein the contour data three-dimensionally represents the contour of said at least part of said subject.

2. The contact avoidance apparatus as recited in claim 1, comprising: a control section for controlling said gantry or said table to avoid contact in a case that there is a risk for said subject to come into contact with said gantry.

3. The contact avoidance apparatus as recited in claim 1, wherein:
    the at least one processing unit generates the contour data representing the contour of said at least part of said subject in a z-direction.

4. The medical apparatus as recited in claim 1, wherein: said sensor section has an imaging section for detecting image data for said subject.

5. The contact avoidance apparatus as recited in claim 4, wherein:
    the at least one processing unit generates the contour data representing the contour of said at least part of said subject as viewed from just above.

6. The contact avoidance apparatus as recited in claim 1, wherein:
    wherein the program further cause the at least one processing unit to calculate a first amount of movement of said cradle in a y-direction and a second amount of movement of said cradle in the z-direction based on a position of a body part to be imaged of said subject, said amounts being for positioning said body part to be imaged at a prespecified position within said gantry.

7. A medical apparatus comprising:
    a gantry;
    a cradle on which a subject to be examined is laid;
    a sensor section for acquiring distance data for determining a distance between said sensor section and at least part of said subject laid on said cradle;
    at least one processing unit; and
    a storage medium with a program stored therein, wherein when the at least one processing unit executes the program the program causes the at least one processing unit to:
        generate contour data representing a contour of said at least part of said subject;
        determine information on positions of points on a body surface of said at least part of said subject with respect to said cradle based on said distance data, and generates said contour data based on said information on positions; and
        decide whether or not there is a risk for said subject to come into contact with said gantry while said gantry or said table is moving based on data representing a limit of a range up to which said subject can come close to said gantry and on said contour data.

8. A computer readable storage medium storing a program applied to a contact avoidance apparatus for avoiding contact of a subject to be examined laid on a cradle with a gantry using distance data for determining a distance between a sensor section and at least part of said subject laid on said cradle, said program being for causing a computer to execute:

contour-data generating processing of generating contour data representing a contour of said at least part of said subject, wherein the contour-data generating processing determines information on positions of points on a body surface of said at least part of said subject with respect to said cradle based on said distance data, and generates said contour data based on said information on positions; and deciding processing of deciding whether or not there is a risk for said subject to come into contact with said gantry while said gantry or said table is moving based on data representing a limit of a range up to which said subject can come close to said gantry and on said contour data;

wherein contour-data generating processing comprises generating the contour data representing the contour of said at least part of said subject in a z-direction.

\* \* \* \* \*